(12) United States Patent
Pritchard

(10) Patent No.: US 7,371,779 B2
(45) Date of Patent: May 13, 2008

(54) SYNERGISTIC COMPOSITIONS OF N-ACYLHOMOSERINE LACTONES AND 4-QUINOLONES

(75) Inventor: David Idris Pritchard, Leicestershire (GB)

(73) Assignee: The Secretary of State for Defense Science and Technology, Salisbury, Wiltshire (GB)

( * ) Notice: Subject to any disclaimer, the term of this patent is extended or adjusted under 35 U.S.C. 154(b) by 570 days.

(21) Appl. No.: 10/481,373

(22) PCT Filed: Jul. 3, 2002

(86) PCT No.: PCT/GB02/03071

§ 371 (c)(1),
(2), (4) Date: May 18, 2004

(87) PCT Pub. No.: WO03/004017

PCT Pub. Date: Jan. 16, 2003

(65) Prior Publication Data

US 2004/0198978 A1    Oct. 7, 2004

(30) Foreign Application Priority Data

Jul. 4, 2001   (GB)   ................. 0116312.0

(51) Int. Cl.
*C07D 31/341*   (2006.01)
(52) U.S. Cl. ...................................... 514/472
(58) Field of Classification Search ................. 514/472
See application file for complete search history.

(56) References Cited

FOREIGN PATENT DOCUMENTS

| WO | WO 95/01175 | 1/1995 |
|---|---|---|
| WO | WO 01/74801 | 10/2001 |
| WO | WO 02/47686 | 6/2002 |
| WO | WO 03/004017 | 1/2003 |

*Primary Examiner*—Taofiq Solola
(74) *Attorney, Agent, or Firm*—Bret E. Field; Bozicevic Field & Francis LLP.

(57) ABSTRACT

A composition having immunosuppressant activity comprises at least one compound of the formula (I) in which R is an acyl group of the formula (II) wherein one of $R^1$ and $R^2$ is H and the other is selected from $OR^4$, $SR^4$ and $NHR^4$, wherein $R^4$ is H or 1-6C alkyl, or $R^1$ and $R^2$ together with the carbon atom to which they are joined form a keto group, and $R^3$ is a straight or branched chain, saturated or unsaturated aliphatic hydrocarbyl group containing from 8 to 11 carbon atoms and is optionally substituted by one or more substituent groups selected from halo, 1-6C alkoxy, carboxy, 1-6C alkoxycarbonyl and $NR^5R^6$ wherein each of $R^5$ and $R^6$ is selected from H and 1-6C alkyl or $R^5$ and $R^6$ together with the N atom form a morpholino or piperazino group, or any enantiomer thereof; and at least one compound of the formula (III): wherein $R^7$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and $NR^{12}R^{13}$, wherein each of $R^{12}$ and $R^{13}$ is independently selected from H and 1-6C alkyl or $R^{12}$ and $R^{13}$ together with the N atom to which they are attached form a saturated heterocyclic group selected from piperidino, piperazino and morpholino; $R^8$ is a group selected from H, —OH, halo, —CHO, —$CO_2H$ and $CONHR^{14}$ wherein $R^{14}$ is H or a 1-6C alkyl; each of $R^9$, $R^{10}$ and $R^{11}$ is independently selected from H, —$CH_3$, —$OCH_3$ and halo; or a non-toxic pharmaceutically-acceptable salt thereof. The determined immunosuppressant activity of the composition is greater than the sum of the activities of the individual components of the composition when determined separately 25 Claims, 15 Drawing Sheets

SYNERGISTIC COMPOSITIONS OF N-ACYLHOMOSERINE LACTONES AND 4-QUINOLONES

The present invention relates to N-acyl homoserine lactones. More particularly, it relates to compositions containing certain N-acyl homoserine lactones together with certain substituted 4-quinolones. It, further, relates to a method of treating a disease responsive to the activity of an immunosuppressant using such compositions.

Immunosuppressant compounds induce an inhibition of the immune response system. Compounds which are known to exhibit immunosuppressant activity include the fungal metabolite Cyclosporin A and the macrolide antibiotic (a metabolite from *Streptomyces tsukabaensis*) termed FK506. Both of these agents have been used clinically and experimentally to suppress the immune system in transplantation and in the treatment of a number of diseases.

Autoimmune diseases are disorders where the host discrimination of "self" versus "non-self" breaks down and the individual's immune system (both acquired and innate components) attacks self tissues. These diseases range from common entities such as rheumatoid arthritis, thyroid autoimmune disease and type 1 diabetes mellitus to less common entities such as multiple sclerosis and to rarer disorders such as myasthenia gravis. Advances in basic biomedical science and, in particular, in immunology have indicated that the main and fundamental lesion responsible for the induction and persistence of most autoimmune diseases resides within auto-reactive proliferating T lymphocytes. In fact, the majority of autoimmune diseases are linked to a loss of T cell homeostasis. The healthy immune system is held in balanced equilibrium, apparently by the contra-suppressive production of cytokines by T helper 1 (Th1) and T helper 2 (Th2) lymphocyte subsets. In autoimmunity, Th1 cytokines predominate; in allergy, Th2 cytokines take their place. A cytokine intimately associated with the development of Th1 biased responses and, consequently, autoimmune disease is TNF-α.

Both Cyclosporin A and FK506 have been used clinically in the treatment of autoimmune diseases with encouraging results.

The currently available immunosuppressant drugs have the disadvantage of a narrow therapeutic index, i.e., toxicity versus clinical benefit. The compounds are known to be nephrotoxic, neurotoxic and potentially diabetogenic and this has limited their use in the fields mentioned above. Problems also exist with the administration of these compounds, their bioavailability and the monitoring of their levels both clinically and in the laboratory.

We disclosed, in WO-A-95/01175, a class of compounds which exhibit antiallergic activity and inhibit the release of histamine, having the generic formula

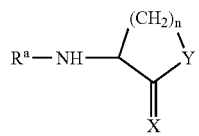

where: n is 2 or 3; Y is O, S or NH; X is O, S or NH; and $R^a$ is $C_1$-$C_{18}$ alkyl or acyl which may be substituted.

Some of these compounds, and methods for their preparation, were previously disclosed in WO-A-92/18614 although that document discloses only that the compounds act as autoinducers and as agents for the control of gene expression. Compounds in the same series are also mentioned in Journal of Bacteriology, volume 175, number 12, June 1993, pages 3856 to 3862 but again there is no teaching that they might have any effect outside micro-organisms.

G. Papaccio, Diabetes Res. Clin. Pract. vol. 13, no. 1, 1991, pages 95-102 discloses the use of N-acetylhomocysteine thiolactone as an enhancer of superoxide dismutase in an attempt to increase protection against chemically induced diabetes.

The use of N-acetylhomocysteine thiolactone to modify the IgE molecule is taught by J. Ljaljevic et al in Od. Med. Nauka, vol.24, 1971, pages 137-143 and Chemical Abstracts, vol.78, no.7, February 1973, abstract no. 41213a. However, there is no suggestion in this paper of immunosuppression or of the inhibition of histamine release.

U.S. Pat. No. 5,591,872 discloses the compound N-(3-oxododecanoyl) homoserine lactone as an autoinducer molecule. In "Infection and Immunity", vol.66, no.1, January 1998, the authors report the action of N-(3-oxododecanoyl) homoserine lactone (OdDHL) in inhibiting the concavalin A mitogen stimulated proliferation of murine spleen cells and TNFα production by LPS-stimulated adherent murine peritoneal macrophages.

In International application no. PCT/GB01/01435 we disclose a subclass of N-acyl homoserine lactones which exhibit an immunosuppressant activity greater than that exhibited by similar compounds outside of the this subclass. The present invention is based on our discovery that the determined immunosuppressant activity of a composition comprising such an N-acyl homoserine lactone together with a member of a group of substituted 4-quinolones is greater than the sum of the activities of the individual components of the composition when determined separately.

BRIEF DESCRIPTION OF FIGS

Figure 4:
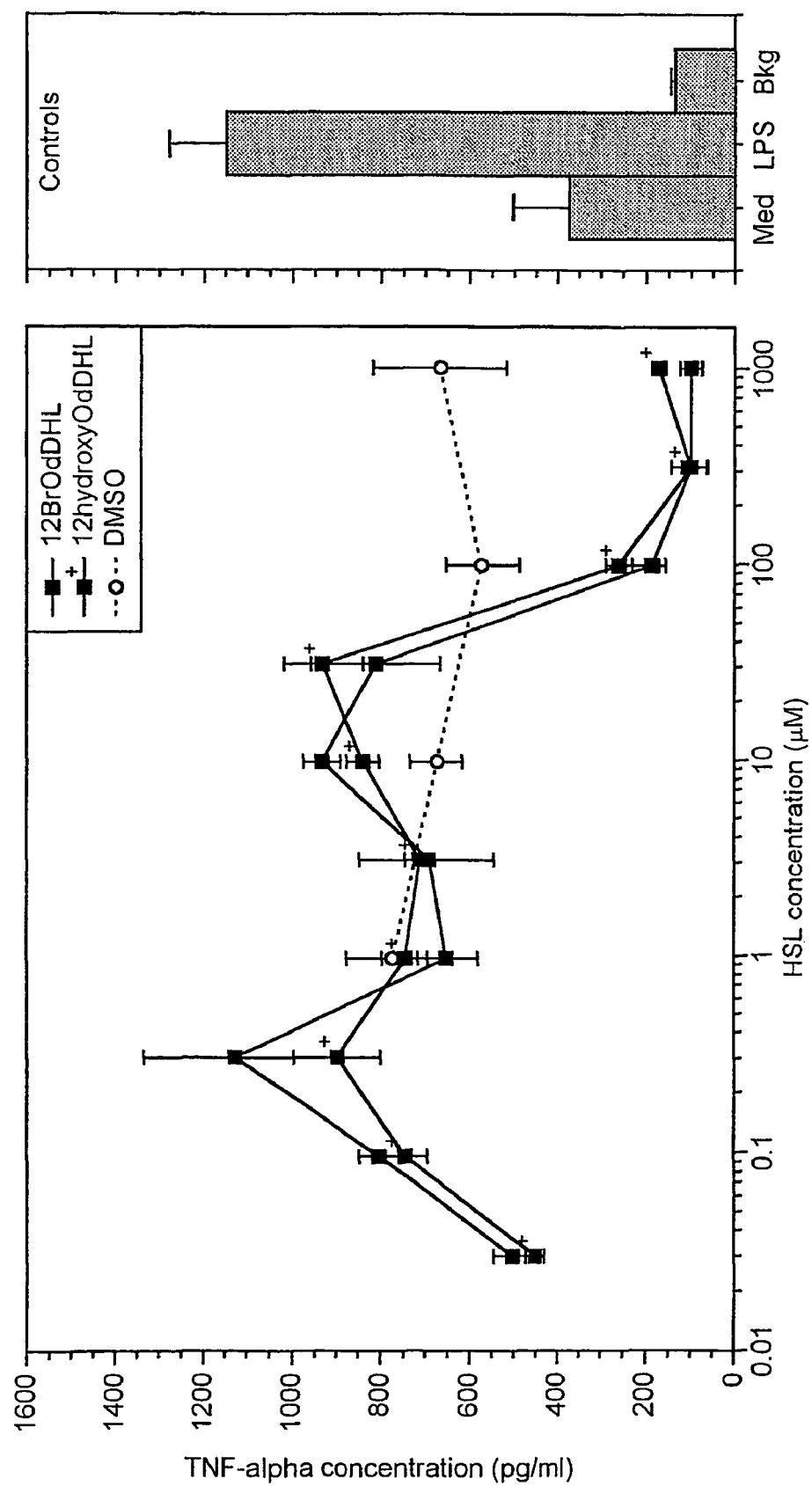

FIG. 4 shows the effect of the of the concentration on lipopolysaccharide (LPS) induced TNF-α production by human peripheral blood mononuclear cells (PBMC) as indicated by plots of TNF-α concentrations (pg/ml) against the concentration (micromolar) of N-(12-bromo-3-oxododecanoyl)-L-homoserine lactone (12BrOdDHL) and N-(12-hydroxy-3-oxododecanoyl)-L-homoserine lactone (12hydroxyOdDHL) and DMSO (vehicle).

Figure 5:
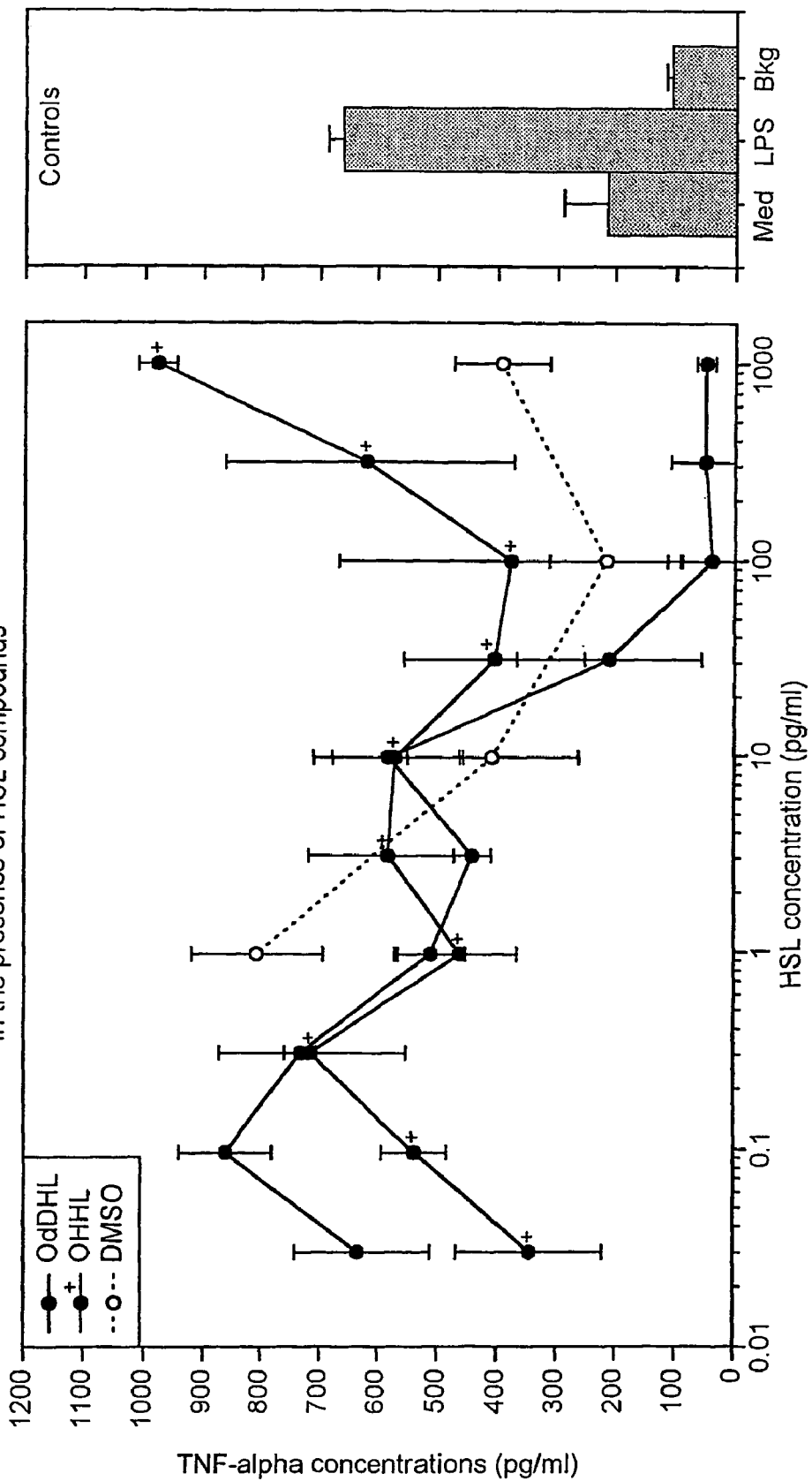

FIG. 5 shows the effect of the of the concentration on lipopolysaccharide (LPS) induced TNF-α production by human peripheral blood mononuclear cells (PBMC) as indicated by plots of TNF-α concentrations (pg/ml) against the concentration (micromolar) of the known shorter side chain compound N-(3-oxohexanoyl)-L-homoserine lactone (OHHL), N-(3-oxododecanoyl)-L-homoserine lactone (OdDHL) and DMSO (vehicle).

Figure 6:
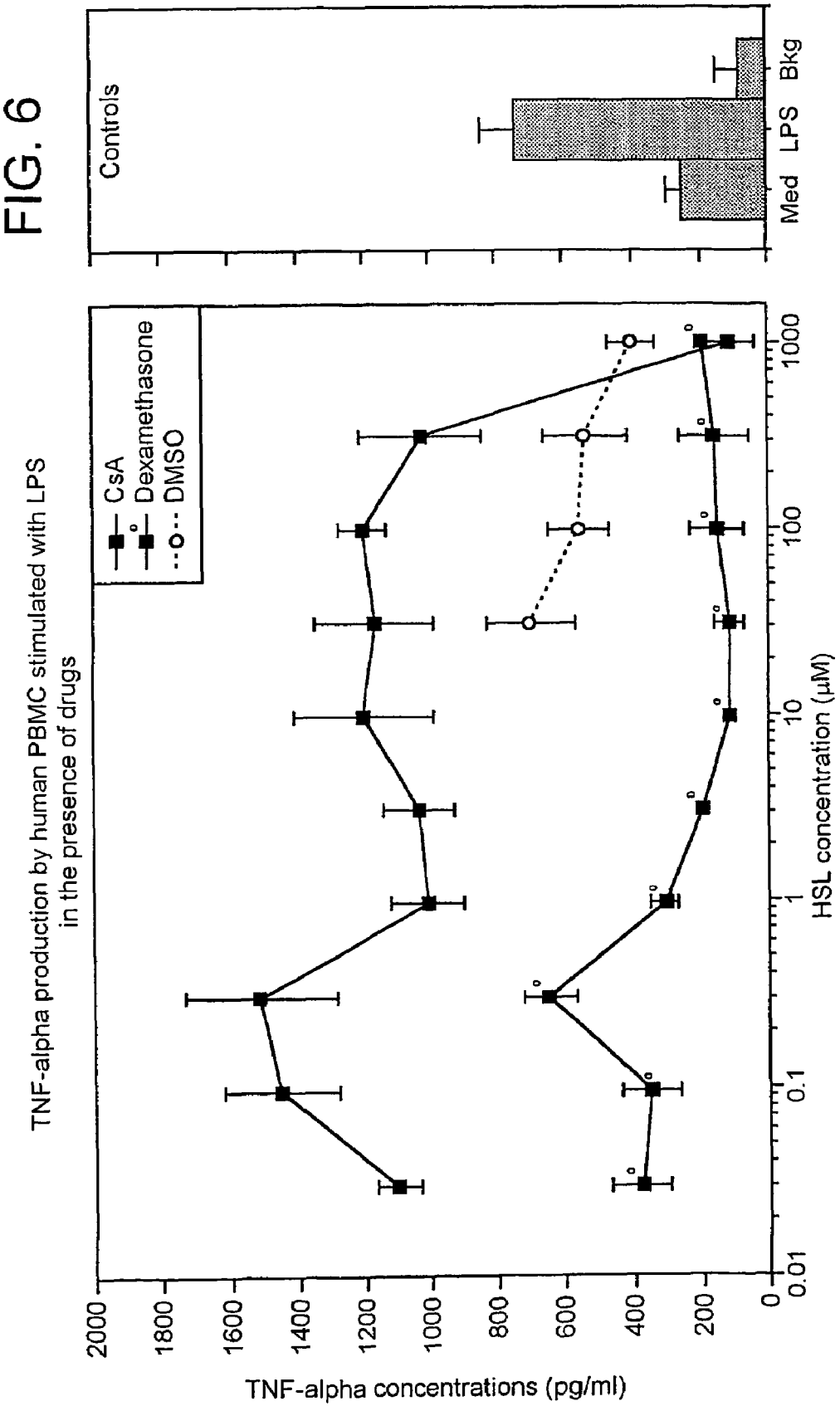

FIG. 6 shows the effect of the of the concentration on lipopolysaccharide (LPS) induced TNF-α production by human peripheral blood mononuclear cells (PBMC) as indicated by plots of TNF-α concentrations pg/ml against the concentration (micromolar) of known drugs dexamethasone and Cyclosporin A (CsA) and DMSO (vehicle).

Figure 7:
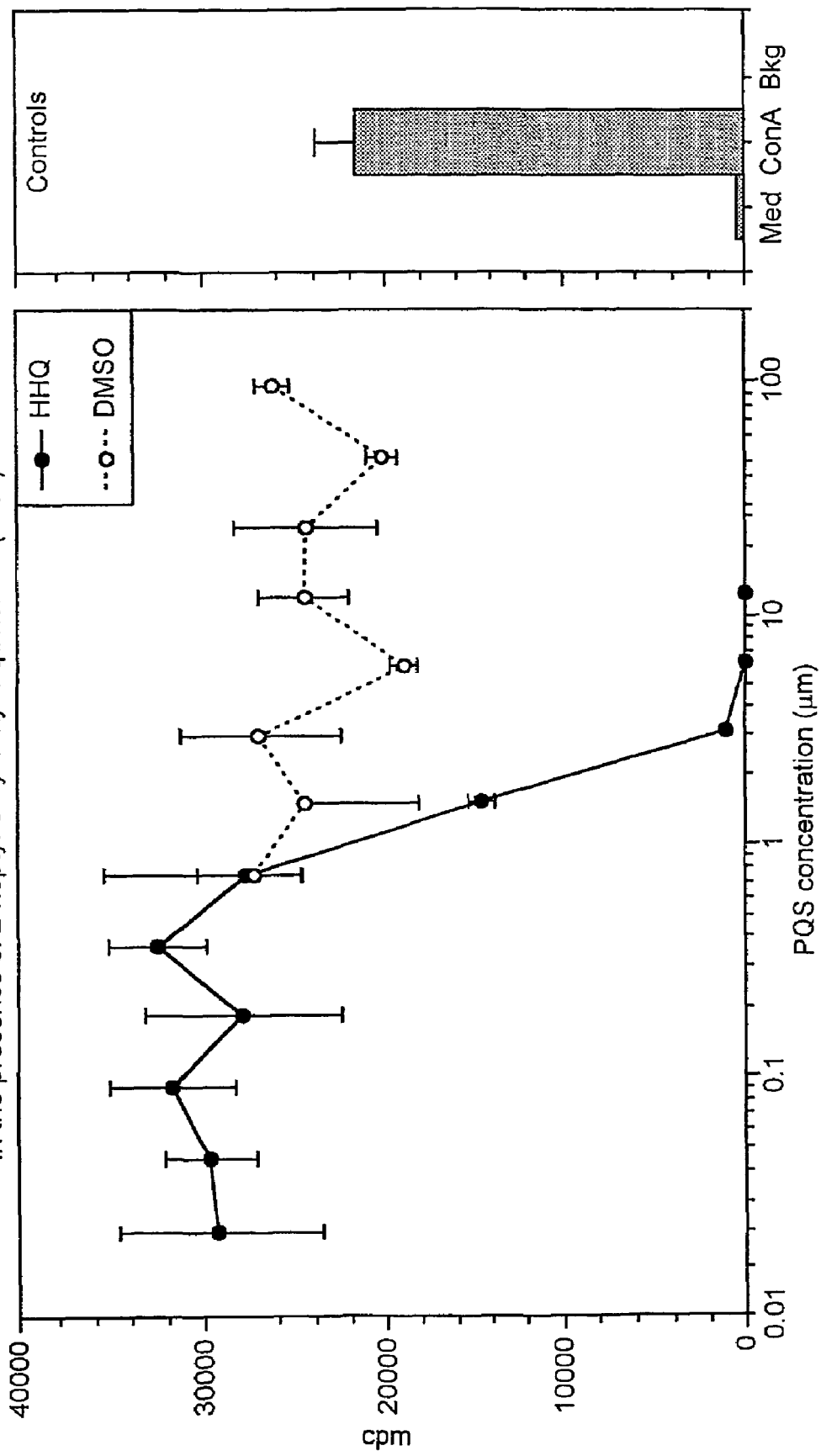

FIG. 7 shows the inhibitory effect on Balb/C splenocyte proliferation as indicated by the plots of counts per minute (cpm) against the concentrations (micromolar) of 2-heptyl-3-hxdroxy-4-quinolone and the vehicle dimethylsulphoxide (DMSO).

Figure 8:
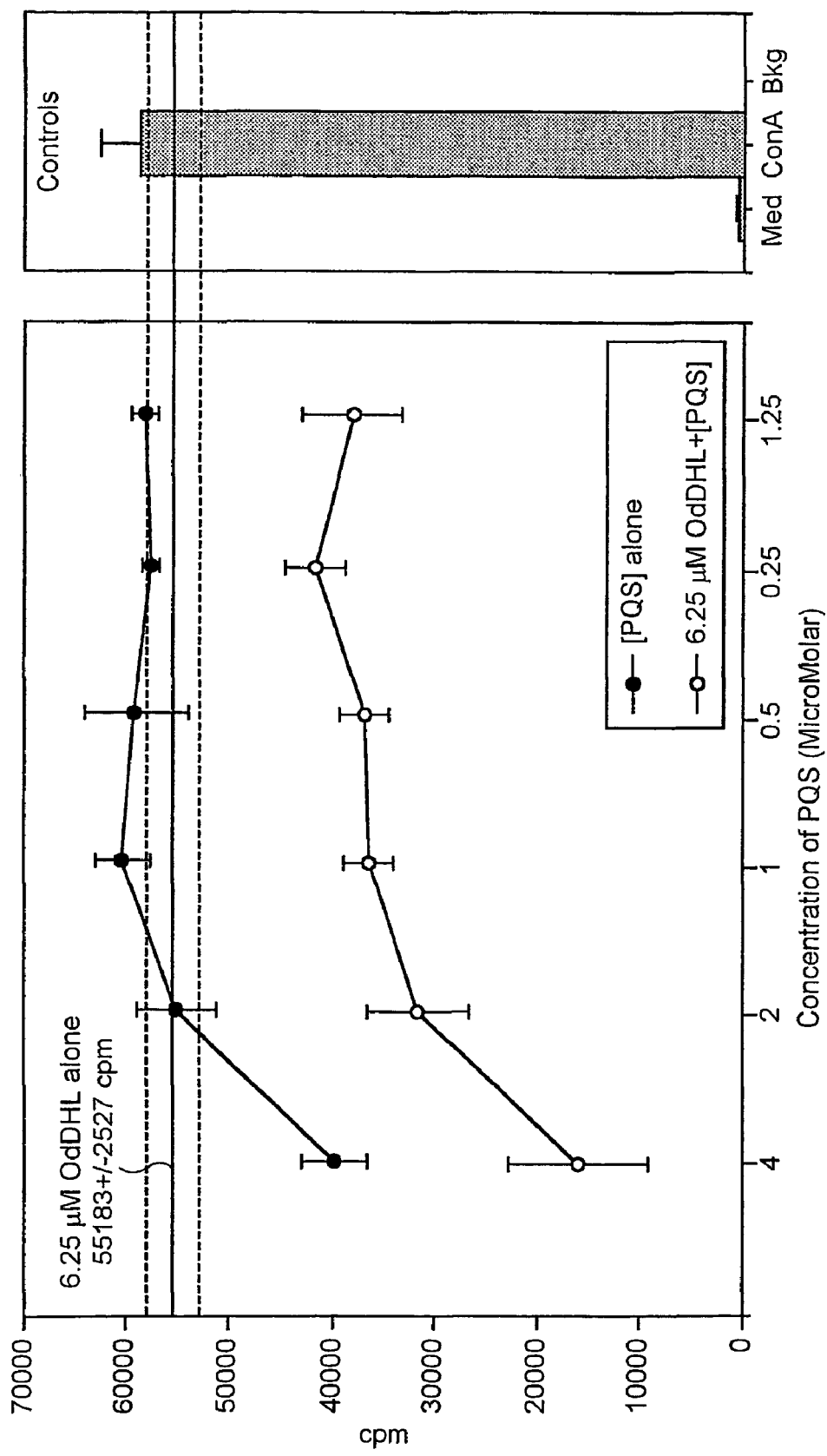

FIG. 8 shows the synergistic inhibitory effect on Balb/C splencocyte proliferation as indicated by the plots of counts per minute (cpm) against the concentrations (micromolar) of 2-heptyl-3-hydroxy-4-quinolone (PQS) alone and 2-heptyl-3-hydroxy-4-quinolone with an inactive concentration of 6.25 μm of N-(3-oxododecanoyl)-L-homoserine lactone (OdDHL).

Figure 9:
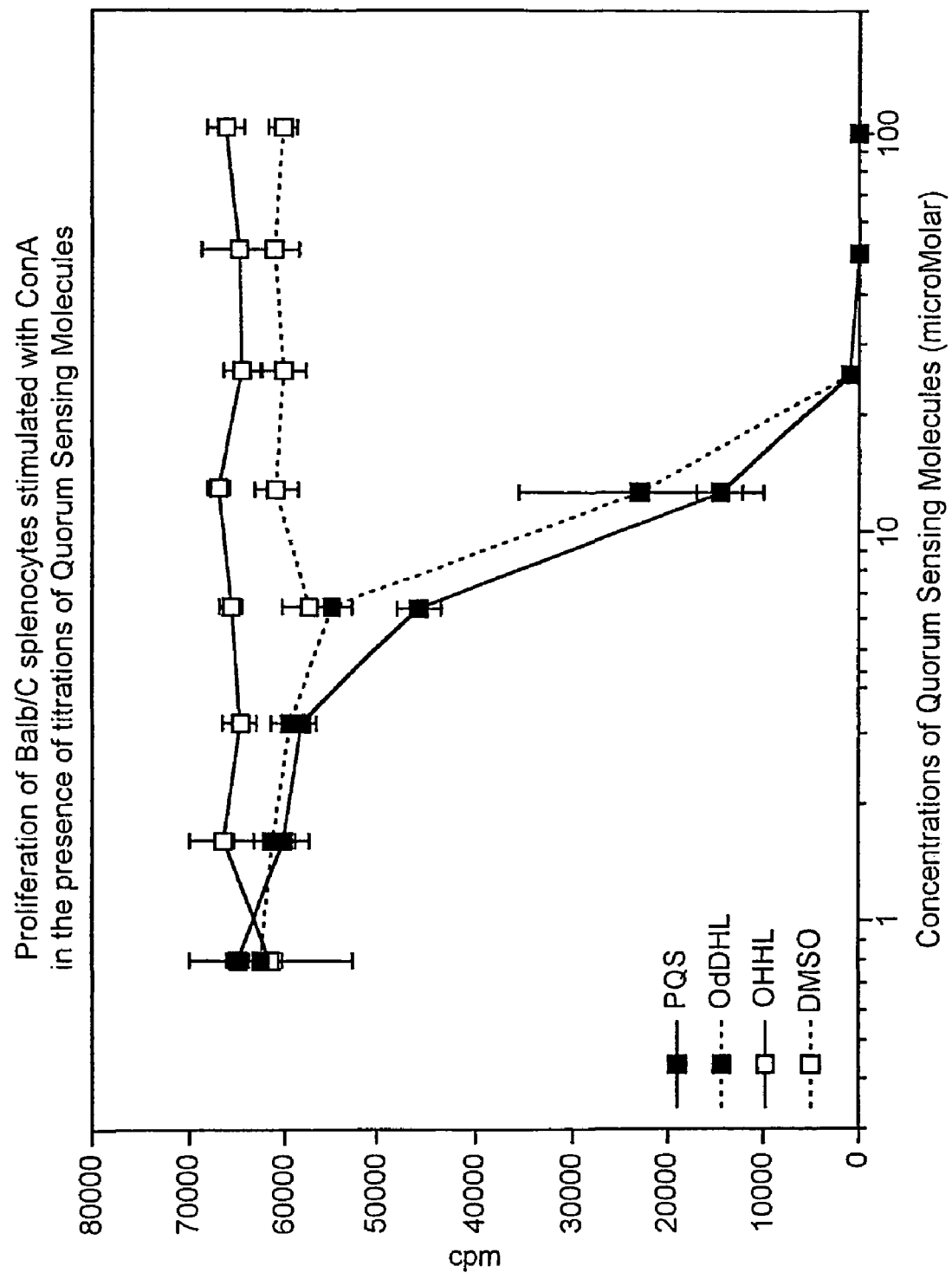

FIG. 9 shows the proliferation of Balb/C splenocytes stimulated with 1 μg/ml Concanavalin A (ConA) in the presence of titrations of Quorum Sensing Molecules as indicated by a plot of counts per minute (cpm) against concentrations of Quorum Sensing Molecules 2-heptyl-3-hydroxy-4-puinolone (PQS), N-(3-oxododecanoyl)-L-homoserine lactone (OdDHL), N-(3-oxohexanoyl)-L-homoserine lactone (OHHL) and DMSO (vehicle).

Figure 10:
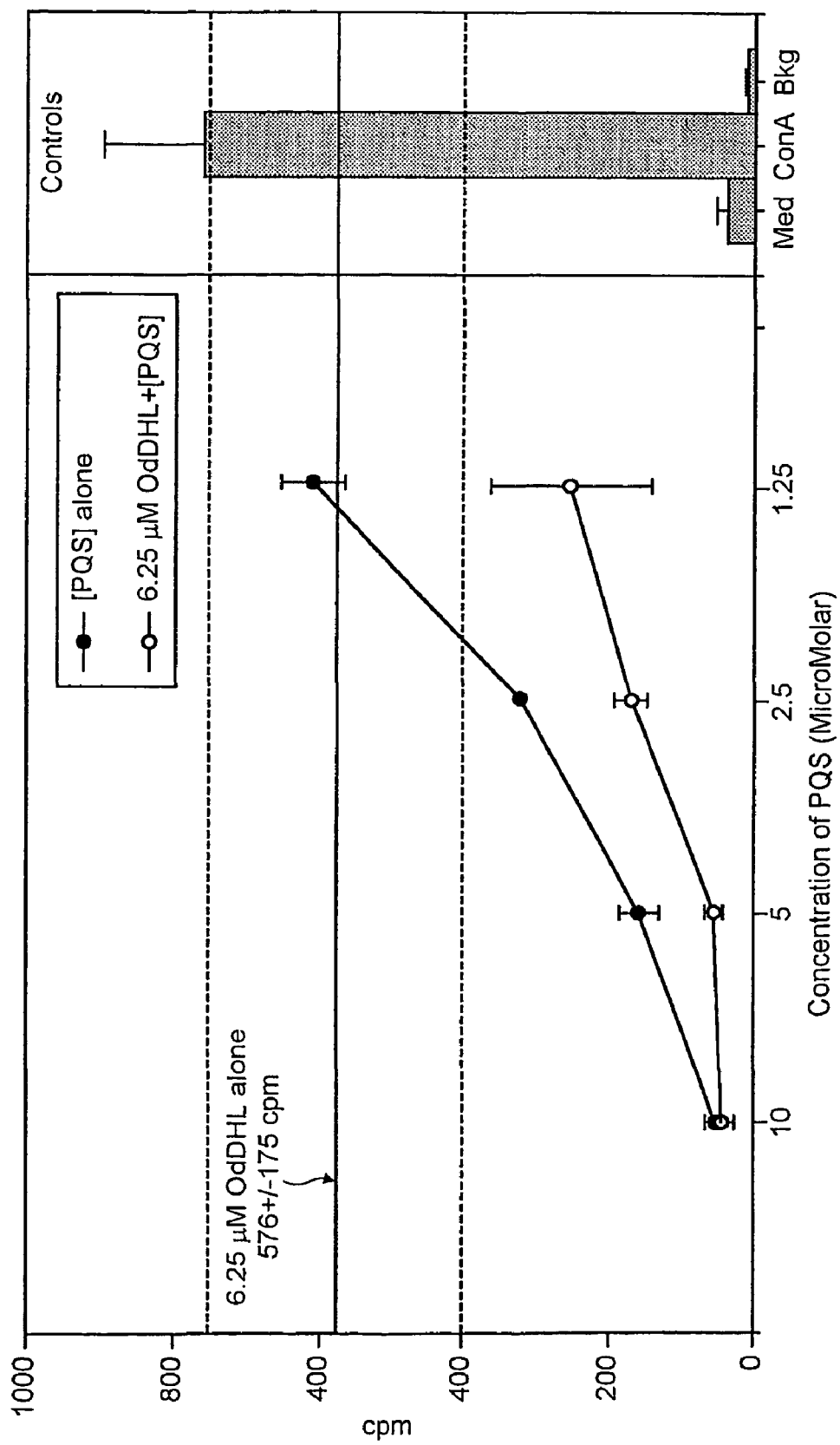

FIG. 10 shows the synergistic inhibitory effect on Balb/C splenocyte stimulated with 1 μg/mI Concanavalin A (ConA) proliferation as indicated by the plots of counts per minute (cpm) against the concentrations (micromolar) of 2-heptyl-3-hydroxy-4-quinolone (PQS) alone and 2-heptyl-3-hy-droxy-4-quinolone with an inactive concentration of 6.25 μm of N -(3-oxododecanoyl)-L-homoserine lactone (OdDHL).

Figure 11:
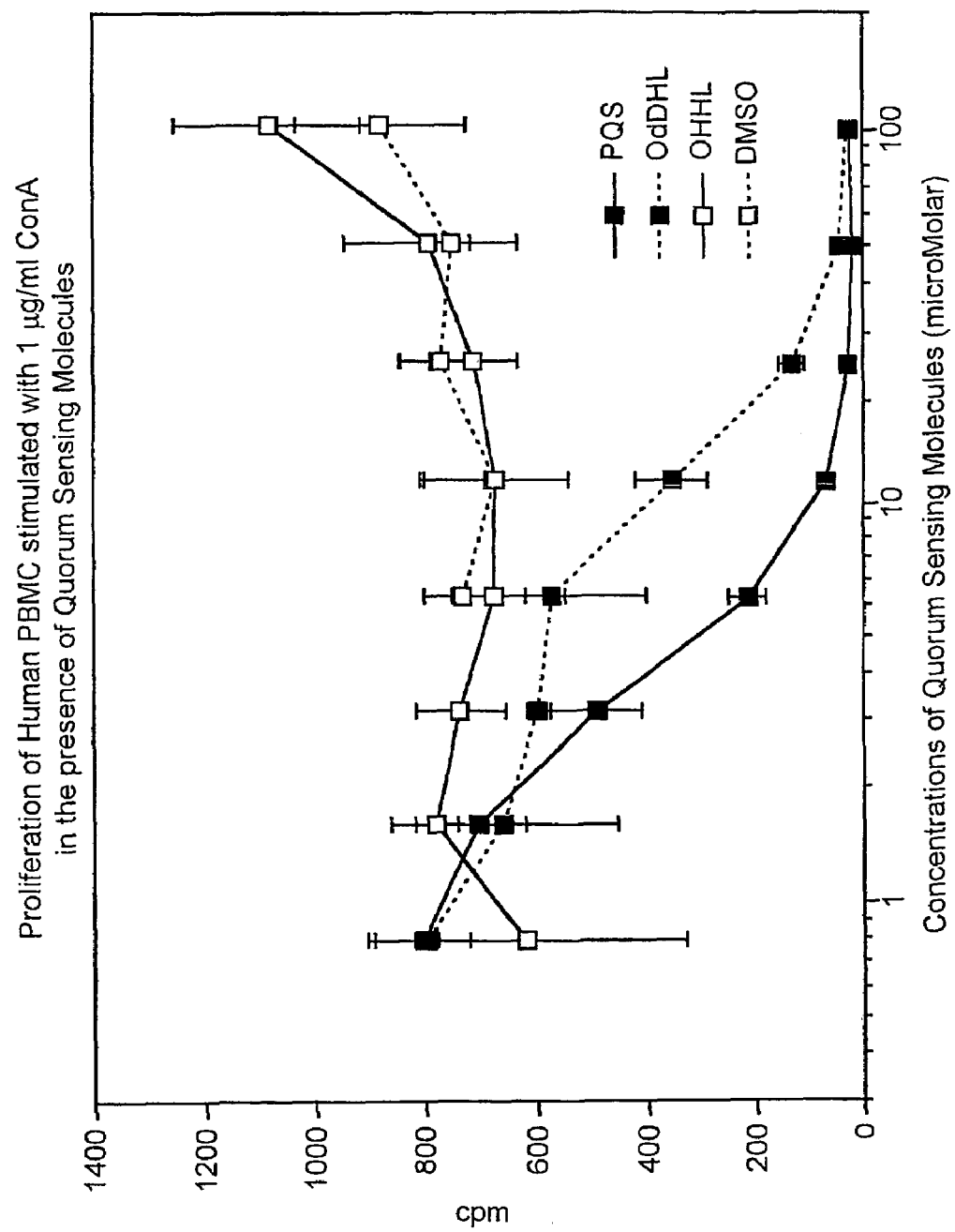

FIG. 11 shows the proliferation human peripheral blood mononuclear cells (PBMC) stimulated with 1 μg/ml Concanavalin A (ConA) in the presence of titrations of Quorum Sensing Molecules as indicated by a plot of counts per minute (cpm) against concentrations of Quorum Sensing Molecules 2-heptyl-3-hydroxy-4-auinolone (PQS), N-(3-oxododecanoyl)-L-homoserine lactone (OdDHL)I N-(3-oxohexanoyl)-L-homoserine lactone (OHHL) and DMSO (vehicle).

Figure 12:
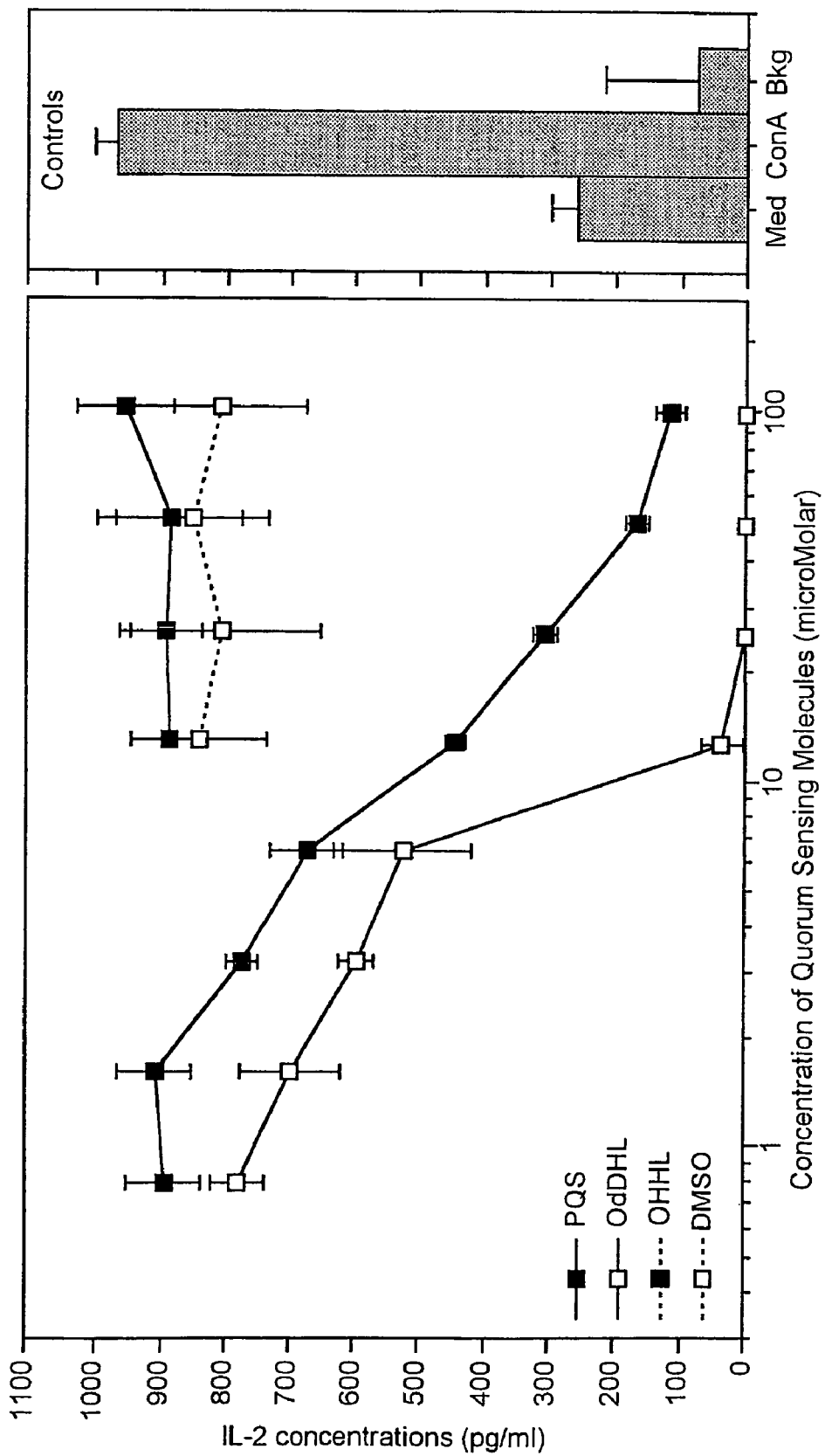

FIG. 12 shows the release of IL-2 from Balb/C splenocytes stimulated with 1 μg/ml Concanavalin A (ConA) as indicated by clots of IL-2 concentrations in pg/ml compared to the concentration (micromolar) of 2-heptyl-3-hydroxy-4-quinolone (PQS), N-(3-oxododecanoyl)-L-homoserine lactone (OdDHL), N-(3-oxohexanoyl)-L-homoserine lactone (OHHL), and DMSO (vehicle).

Figure 13:
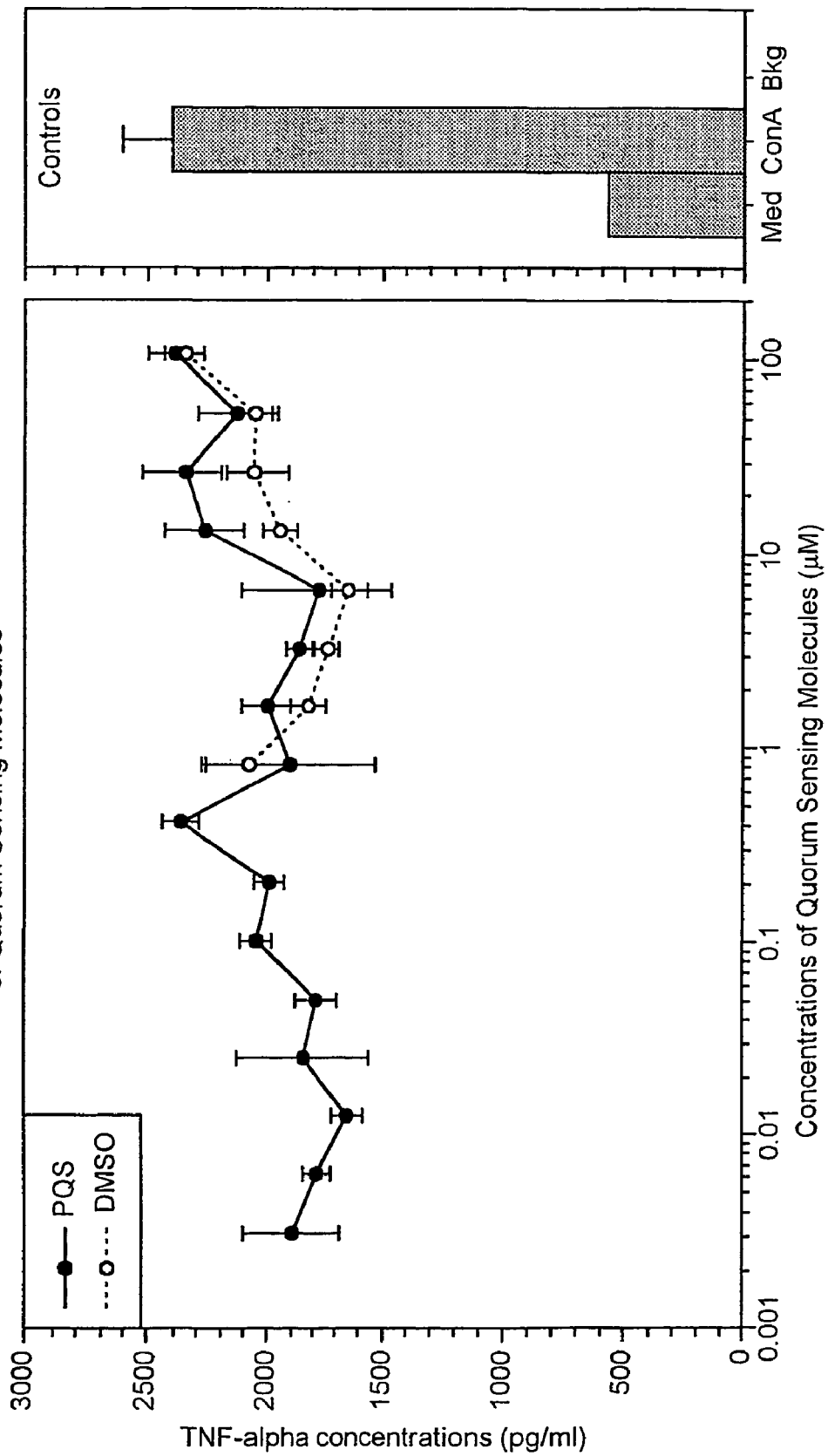

FIG. 13 shows the release of TNF-α from human peripheral blood mononuclear cells (PBMC) stimulated lipopolysaccharide (LPS) as indicated by plots of TNF-α concentrations (pg/ml) against the concentration (micromolar) of 2-heptyl-3-hxdroxy-4-quinolone (PQS) and DMSO (vehicle).

Figure 14:
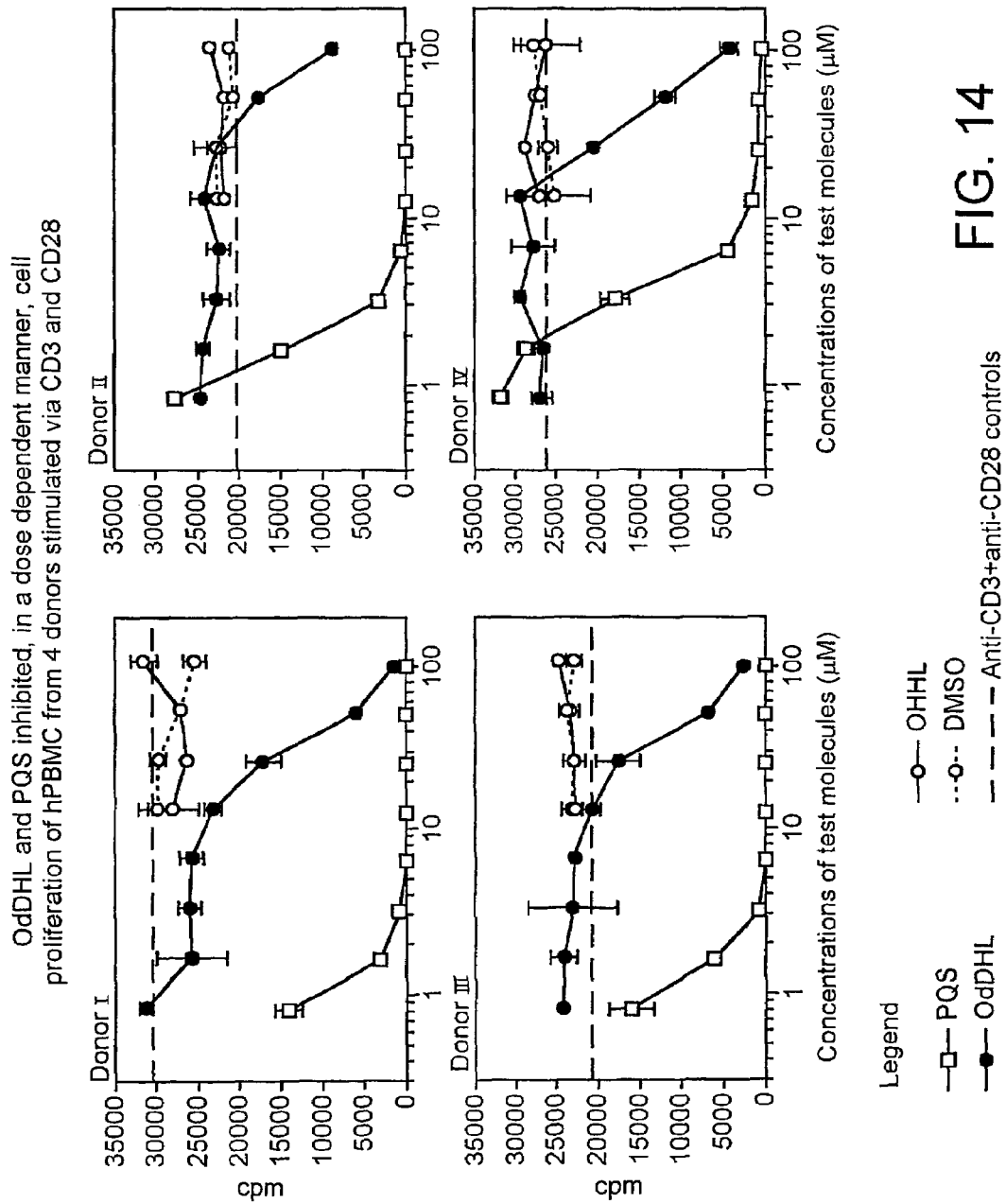

FIG. 14 shows the dose dependent inhibitory effect of h peripheral blood mononuclear cells (PBMC) proliferation by the Quorum sensing molecules 2-heptyl-3-hydroxy-4-quinolone (PQS), N-(3-oxododecanoyi)-L-homoserine lactone (OdDHL), N-(3-oxohexanoyl)-L-homoserine lactone (OHHL), and DMSO (vehicle) in Donors I, II, III, and IV indicated by plots of TNF-α concentrations (pg/ml) against the concentration (micromolar) of PQS, OdDHL, OHHL and DMSO (vehicle).

Figure 15:
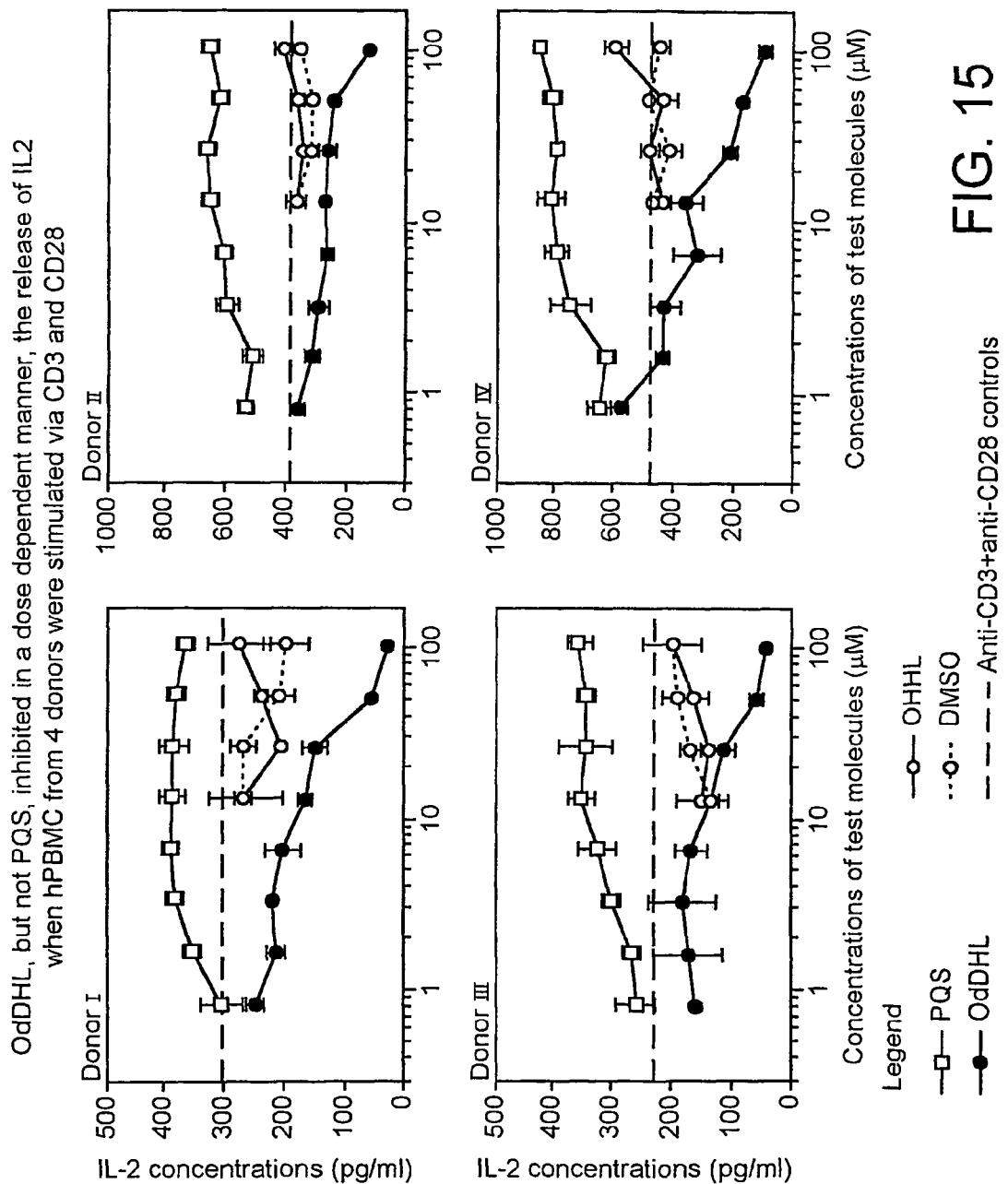

FIG. 15 shows the inhibition of the release of IL-2 by the Quorum sensing molecules 2-heptyl-3-hydroxy-4-quinolone (PQS), N-(3-oxododecanoyl)-L-homoserine lactone (OdDHL), N-(3-oxohexanoyl)-L-homoserine lactone (OHHL), and DMSO (vehicle) in Donors I, II, III, and IV indicated by clots of IL-2 concentrations (pg/ml) against the concentration (micromolar) of PQS, OdDHL, OHHL and DMSO.

DETAILED DESCRIPTION

According to the present invention there is provided a composition comprising at least one compound of the formula I

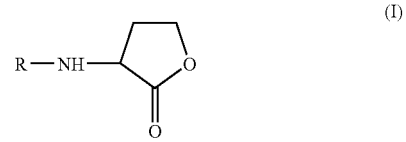

in which R is an acyl group of the formula II

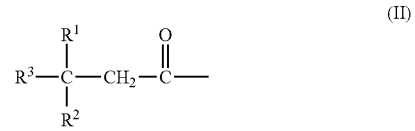

wherein one of $R^1$ and $R^2$ is H and the other is selected from $OR^4$, $SR^4$ and $NHR^4$, wherein $R^4$ is H or 1-6C alkyl, or $R^1$ and $R^2$ together with the carbon atom to which they are joined form a keto group, and $R^3$ is a straight or branched chain, saturated or unsaturated aliphatic hydrocarbyl group containing from 8 to 11 carbon atoms and is optionally substituted by one or more substituent groups selected from halo, 1-6C alkoxy, carboxy, 1-6C alkoxycarbonyl and $NR^5R^6$ wherein each of $R^5$ and $R^6$ is selected from H and 1-6C alkyl or $R^5$ and $R^6$ together with the N atom form a morpholino or piperazino group, or any enantiomer thereof, together with at least one compound of the formula III

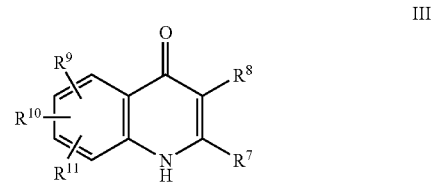

wherein $R^7$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and $NR^{12}R^{13}$, wherein each of $R^{12}$ and $R^{13}$ is independently selected from H and 1-6C alkyl or $R^{12}$ and $R^{13}$ together with the N atom to which they are attached form a saturated heterocyclic group selected from piperidino, piperazino and morpholino; $R^8$ is a group selected from H, —OH, halo, —CHO, —$CO_2H$ and $CONHR^{14}$ wherein $R^{14}$ is H or a 1-6C alkyl; each of $R^9$, $R^{10}$ and $R^{11}$ is independently selected from H, —$CH_3$, —$OCH_3$ and halo; or a non-toxic pharmaceutically-acceptable salt thereof.

In a second aspect the present invention provides a method of treating a disease of living animal body, including a human, which disease is responsive to the activity of an immunosuppressant which method comprises administering to the living animal body, including a human, at least one compound of the formula I, as defined herein, and at least one compound of the formula III, as defined herein.

The N-acyl homoserine lactones of the formula I above are capable of modulating the immune response in the living animal body, including human. In particular, they have an inhibitory effect on lymphocyte proliferation in humans and down-regulate TNF-α secretion by monocytes/macrophages and, in consequence, the activation of Th1 lymphocytes in humans.

In the compounds of the general formula I given above, the group R has the formula II

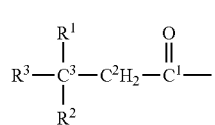

In formula II according to a first preferred embodiment one of $R^1$ and $R^2$ is H and the other is selected from $OR^4$, $SR^4$ and $NHR^4$, in which $R^4$ is H or a 1-6C alkyl group. Preferably, $R^4$ is H. Such a definition of $R^1$ and $R^2$ gives rise to chirality at the carbon atom to which $R^1$ and $R^2$ are attached (C-3). The compounds of the invention can, thus, be in the form of racemates, optically active isomers or mixtures thereof. According to a particular preferred embodiment one of $R^1$ and $R^2$ is H and the other is OH.

According to this first preferred embodiment the group $R^3$ in formula II is a straight or branched chain 8 to 11C aliphatic hydrocarbyl group which is saturated or which may be ethylenically unsaturated. The group may, further, be substituted by one or more substituent groups selected from halo, for example F, Cl, Br or I; 1-6C alkoxy, for example methoxy, ethoxy, n-propoxy, iso-propoxy, n-butoxy, iso-butoxy and tert-butoxy; carboxy including salts thereof, 1-6C alkoxycarbonyl, for example methoxycarbonyl, carbamoyl, for example N,N-dimethylcarbamoyl and $NR^5R^6$, wherein $R^5$ and $R^6$ are each selected from H and 1-6C alkyl or $R^5$ and $R^5$ together with the nitrogen atom to which they are attached form a morpholino group or a piperazino ring, optionally substituted at the 4-N by a methyl group. A particularly preferred $R^3$ group in formula II above is a straight chain or branched chain 8 to 11C alkyl group which is optionally substituted by one substituent selected from Br, carboxy including salts thereof, and methoxycarbonyl. The substituent is typically, though not necessarily, attached in a terminal position on the alkyl group. Alternatively, the $R^3$ group is a straight chain or branched chain 8-11C alkenyl group, preferably monoethenically unsaturated, which may be substituted by a substituent selected from Br, carboxy including a salt thereof, and methoxycarbonyl. Again, the substituent is typically, though not necessarily, attached in a terminal position on the alkenyl group.

In formula II above according to a second preferred embodiment the groups $R^1$ and $R^2$ together form an oxo group (═O) such that a keto group exists at the C-3 position in the acyl group. In such a case the group $R^3$ in formula II will typically be an optionally-substituted, saturated or ethylenically-unsaturated, straight or branched chain 8 to 11C aliphatic hydrocarbyl group.

In the case where the group $R^3$ is substituted, it will be substituted by one or more substituent groups selected from halo, for example F, Cl, Br or I; 1-6C alkoxy, for example methoxy, ethoxy, n-propoxy, iso-propoxy, n-butoxy, iso-butoxy and tert-butoxy; carboxy including salts thereof, 1-6C alkoxycarbonyl, for example methoxycarbonyl, carbamoyl, for example N,N-dimethylcarbamoyl, and $NR^5R^6$, wherein $R^5$ and $R^6$ are each selected from H and 1-6C alkyl or $R^5$ and $R^8$ together with the nitrogen atom to which they are attached form a morpholino group or a piperazino ring, optionally substituted at the 4-N by a methyl group.

According to one preferred embodiment the $R^3$ group in formula II above is a straight chain or branched chain 8, 9, 10 or 11C alkyl group which is optionally substituted by one substituent selected from Br, carboxy including salts thereof, and methoxycarbonyl. The substituent, if present, is typically, though not necessarily, attached in a terminal position on the alkyl group.

According to yet another preferred embodiment the $R^3$ group is a straight chain or branched chain 8-11C alkenyl group, preferably monoethenically unsaturated, which may be substituted by a substituent selected from Br, carboxy including a salt thereof, and methoxycarbonyl. The substituent is typically, though not necessarily, attached in a terminal position on the alkenyl group.

Examples of acyl groups R of formula II above in which $R^3$ is a saturated hydrocarbyl group include:—
  3-oxoundecanoyl;
  11-bromo-3-oxoundecanoyl;
  10-methyl-3-oxoundecanoyl;
  6-methyl-3-oxoundecanoyl;
  3-hydroxydodecanoyl;
  12-bromo-3-oxododecanoyl;
  3-oxododecanoyl;
  3-oxotridecanoyl;
  ? 3-bromo-3-oxododecanoyl;
  3-hydroxytetradecanoyl;
  3-oxotetradecanoyl;
  14-bromo-3-oxotetradecanoyl; and
  13-methoxycarbonyl-3-oxotridecanoyl.

Examples of acyl groups R of formula II above in which $R^3$ is an ethylenically unsaturated hydrocarbyl group include:—
  3-oxo-12-tridecenoyl;
  3-oxo-7-tetradecenoyl;
  3-hydroxy-7-tetradecenoyl;
  3-oxo-9-tetradecenoyl;
  3-hydroxy-9-tetradecenoyl;
  3-oxo-10-tetradecenoyl;
  3-hydroxy-10-tetradecenoyl;
  3-oxo-11-tetradecenoyl;
  3-hydroxy-11-tetradecenoyl;
  3-oxo-13-tetradecenoyl; and
  3-hydroxy-13-tetradecenoyl.

The compound having the formula I above is preferably N-(3-oxododecanoyl) homoserine lactone or an enantiomer thereof.

The compounds of the present invention having the 3-oxo group may, in general, be prepared by a method comprising the steps of:

(1) reacting an acid having the general formula $R^3COOH$, where $R^3$ is as defined above, with Meldrum's acid (2,2-dimethyl-1,3-dioxane-4,6-dione) in the presence of 4-dimethylaminopyridine and N,N$^1$-dicyclohexyl-carboxdiimide in a dry organic solvent, such as dry dichloromethane, to give the acylated Meldrum's acid; and (2) reacting the acylated Meldrum's acid with L-homoserine lactone hydrochloride in an organic solvent, e.g., acetonitrile, to give the N-(3-oxoacylated)-L-homoserine lactone.

Where the appropriate acid is not available it may be prepared by, for instance, oxidising the appropriate alcohol using chromic acid.

The corresponding N-(3-hydroxyacylated)-L-homoserine lactone may be prepared by reducing the N-(3-oxoacylated)-L-homoserine lactone using sodium cyanoborohydride in acid conditions.

The compounds having the general formula III given above include their non-toxic pharmaceutically-acceptable salts. The group $R^7$ in formula I is a straight or branched chain 1 to 18C, preferably 3 to 13C, hydrocarbyl group which may be saturated or which may be ethnically unsaturated. This group may, optionally, be substituted by one or more substituents groups selected from halo, for example, F, Cl, Br or I; 1-6C alkoxy, for example methoxy, ethyoxy, n-propoxy, iso-propoxy, n-butoxy, isobutoxy and tert-butoxy; carboxy including non-toxic salts thereof; 1-6C alkoxycarbonyl, for example methoxycarbonyl; and $NR^{12}R^{13}$ wherein each of $R^{12}$ and $R^{13}$ is independently selected from H and 1-6C alkyl, for example methyl or ethyl. $R^{12}$ and $R^{13}$, together with the N atom to which they are attached may, alternatively, form a piperidino moiety, a morpholino moiety or a piperazino moiety in which the 4-N atom may, optionally, be substituted by a methyl group.

Typically, the hydrocarbyl group $R^7$ will be a straight chain alkyl group having from 3 to 13 carbon atoms, for example, propyl, n-pentyl, n-heptyl, n-nonyl and n-undecyl, which may optionally be substituted as described above. Preferably, in the formula I above the group $R^7$ will be n-heptyl.

The group $R^8$ is selected from H, —OH, halo, for example F, Cl, Br and 1, CHO, $CO_2H$ and $CONHR^{14}$ wherein $R^{14}$ is H or 1-6C alkyl. In the case where $R^8$ is a carboxylic acid group the scope of the invention includes the non-toxic metal and ammonium salts of the carboxylic acid. Preferably, however the group $R^8$ is OH. Each of the groups $R^9$, $R^{10}$ and $R^{11}$ is independently selected from H, $CH_3$, $OCH_3$ and halo, for example F, Cl, Br and I. Thus $R^9$, $R^{10}$ and $R^{11}$ may be the same or different groups. Any of the $R^9$, $R^{10}$ and $R^{11}$ groups may be attached to any of the free ring positions on the fused benzene ring of the quinolones, i.e., at ring positions 5, 6, 7 and 8. Preferably, when not all of the $R^9$, $R^{10}$ and $R^{11}$ are H, substitution on the quinolone structure will be at position 6, 7 or both. More preferably, however, all of $R^9$, $R^{10}$ and $R^{11}$ are H, i.e., the fused benzene ring of the quinolone is unsubstituted. Examples of compounds of formula III are shown below.

Examples of Compounds of the Formula III

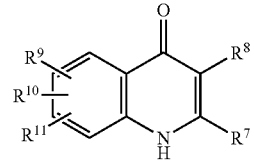

(I)

| Compound No. | $R^7$ | $R^8$ | $R^9$ | $R^{10}$ | $R^{11}$ |
|---|---|---|---|---|---|
| 1 | $(CH_2)_2CH_3$ | OH | H | H | H |
| 2 | $(CH_2)_4CH_3$ | OH | H | H | H |
| 3 | $(CH_2)_6CH_3$ | OH | H | H | H |
| 4 | $(CH_2)_8CH_3$ | OH | H | H | H |
| 5 | $(CH_2)_{10}CH_3$ | OH | H | H | H |
| 6 | $(CH_2)_6COOH$ | OH | H | H | H |
| 7 | $(CH_2)_6CH_3$ | H | H | H | H |
| 8 | $(CH_2)_6CH_3$ | CHO | H | H | H |
| 9 | $(CH_2)_6CH_3$ | Cl | H | H | H |
| 10 | $(CH_2)_6CH_3$ | COOH | H | H | H |
| 11 | $(CH_2)_6CH_3$ | $CONH_2$ | H | H | H |
| 12 | $(CH_2)_6CH_3$ | $CONHCH_3$ | H | H | H |
| 13 | $(CH_2)_6CH_3$ | OH | 6-Me | H | H |
| 14 | $(CH_2)_6CH_3$ | OH | 7-Me | H | H |
| 15 | $(CH_2)_6CH_3$ | OH | 6-OMe | H | H |
| 16 | $(CH_2)_6CH_3$ | OH | 7-OMe | H | H |
| 17 | $(CH_2)_6CH_3$ | OH | 6-Me | 7-Me | H |
| 18 | $(CH_2)_6CH_3$ | OH | 6-OMe | 7-OMe | H |

As mentioned above, the compounds of the general formula I have use as pharmaceutically-active ingredients in the treatment of an animal body, including the human body, suffering from a disease or disorder which is responsive to the activity of an immunosuppressant, particularly for the treatment of an autoimmune disease, such as psoriasis, multiple sclerosis and rheumatoid arthritis.

The compounds having the general formula III above, including non-toxic salts thereof, are, themselves, capable of modulating the immune response in the living animal body, including the human body. In particular, we believe that these compounds have an inhibitory effect on lymphocyte proliferation in humans.

The present invention is based on experimental results from studies carried out on murine and on human systems which show that cell proliferation in the presence of an inactive concentration of a compound of the formula I above is synergistically inhibited when a suboptimal concentration of a compound of the formula III is added to the system. For this reason, it appears that the inhibition of cell proliferation by a combination of a compound of the formula I and a compound of the formula III is greater than the sum of the individual effects of each of the compounds when used separately.

We believe that a composition according to the present invention has use in the treatment of diseases or disorders in the animal body, including human, which are responsive to the activity of an immunosuppressant for instance in the treatment of an autoimmune disease such as psoriasis, multiple sclerosis and rheumatoid arthritis. The dosages of the compounds in the composition which is administered to the animal body in need of therapy will, of course, depend on the actual active compounds used, the mode of treatment employed and the type of treatment desired as well as on the body mass of the patient. It will be clear that a combination treatment employing a compound of the formula I above and a compound of the formula III above may be carried out by administering the compounds together in the form of a composition containing both or, alternatively, by administering each compound one after the other such that a combination treatment occurs within the body, or at the body site, being treated. The active compounds can be administered on their own or in the form of an appropriate medicinal composition containing, for instance, an appropriate pharmaceutical carrier or diluent. Other substances may, of course, also be employed in such medicinal compositions, such as antioxidants and stabilisers, the use of which are well known in the art. In the treatment of psoriasis, the active compounds will, typically, be formulated for topical application to the patient, for instance in the form of an ointment, cream or lotion. It is also believed that the compounds described herein can also be used in a vaccine preparation as an adjuvant, in situations where enhanced Th2 responses would be beneficial, for example when vaccinating against worm infection in humans or domestic or husbanded animals.

EXAMPLES

Example 1

N-(3-oxoundecanoyl)-L-homoserine lactone (OuDHL)

To a solution of nonanoic acid (2 mmol) in dry dichloromethane (20 ml) was added 4-dimethylaminopyridine (2.1 mmol), N,N'-dicyclohexylcarbodiimide (2.2 mmol) and Meldrum's acid (2 mmol). The solution was stirred at room temperature overnight and then filtered to remove the precipitated dicyclohexylurea. The filtrate was evaporated to dryness and the residue redissolved in ethyl acetate. The ethyl acetate solution was washed with 2M hydrochloric acid, dried over anhydrous magnesium sulphate and concentrated to afford the nonanoyl Meldrum's acid.

To a stirred solution of the nonanoyl Meldrum's acid (1 mmol) in acetonitrile (30 ml) was added L-homoserine lactone hydrochloride (1 mmol) and triethylamine (1.2 mmol). The mixture was stirred for 2 h and then refluxed for a further 3 h. The solvent was removed by rotary evaporation to give a residue that was redissolved in ethyl acetate. The organic solution was sequentially washed with saturated sodium hydrogen carbonate solution, 1M potassium hydrogen sulphate solution and saturated sodium chloride solution. After drying over anhydrous magnesium sulphate, the organic extract was evaporated to dryness and the residue purified by preparative layer chromatography on silica plates.

Spectral Data

N-(3-Oxoundecanoyl)-L-homoserine lactone $^1$H NMR (250 MHz, CDCl$_3$) δ 0.9 (3H, t, CH$_3$), 1.27 (10H, m, CH$_3$(CH$_2$)$_5$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 50β-H), 4.58 (1H, m, 3-H), 7.64 (1H, d, NH).

The procedure described above in Example 1 was followed to prepare other N-(3-oxoacylated)-L-homoserine lactones as described below using, in each case, the appropriate carboxylic acid.

Example 2

N-(11-Bromo-3-oxoundecanoyl)-L-homoserine lactone (11Br OuDHL)

ES-MS m/z 362.2 & 364.2 (MH+, C$_{15}$H$_{25}$NO$_4$Br requires m/z 362 & 364); $^1$H NMR (250 MHz, CDCl$_3$) δ 1.27 (8H, m, BrCH$_2$CH$_2$(CH$_2$)$_4$), 1.45 (2H, m, BrCH$_2$CH$_2$CH$_2$) 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 3.53 (2H, t, BrCH$_2$) 4.27 (1H, m, 5α-H), 4.48 (1H td, 5β-H), 4.58 (1H, m, 3-H), 7.64 (1H, d, NH).

Example 3

N-(10-Methyl-3-oxoundecanoyl)-L-homoserine lactone (10MeOuDHL)

ES-MS m/z 298.0 (MH+, C$_{16}$H$_{28}$NO$_4$ requires m/z 298.0); $^1$H NMR (90 MHz, CDCl$_3$) δ 0.8 (6H, d, (CH$_3$)$_2$CH), 1.2 (9H, m, CH(CH$_2$)$_4$), 1.7 (2H, m, CH$_2$CH$_2$CO), 2.2 (1H, m, 4α-H), 2.45 (2H, t, CH$_2$CO), 2.65 (1H, m, 4β-H), 3.4 (2H, s, COCH$_2$CO), 4.0-4.8 (3H, m, 5α-H, 5β-H, 3-H), 7.65 (1H, d, NH).

Example 4

N-(10-Methoxycarbonyl-3-oxodecanoyl)-L-homoserine lactone (10(MeO$_2$C)ODHL)

ES-MS m/z 328.3 (MH+, C$_{16}$H$_{26}$NO$_6$ requires m/z 328); $^1$H NMR (250 MHz, CDCl$_3$) δ 1.27 (6H, m, CH$_3$OCOCH$_2$CH$_2$(CH$_2$)$_3$), 1.59 (4H, m, CH$_2$CH$_2$CO & CH$_3$OCOCH$_2$CH$_2$), 2.22 (1H, m, 4α-H), 2.25 (2H, t, CH$_3$OCOCH$_2$), 2.52 (2H, t, CH$_2$CO), 2.76 (1H, m, 4β-H), 3.47 (2H, s, COCH$_2$CO), 3.58 (3H, s, CH$_3$O), 4.27 (1H, m, 5α-H), 4.48 (1H, td, 5β-H), 4.58 (1H, m, 3-H), 7.64 (1H, d, NH).

Example 5

N-(6-Methyl-3-oxoundecanoyl)-L-homoserine lactone (6MeOuDHL)

ES-MS m/z 298.2 (MH+, C$_{16}$H$_{28}$NO$_4$ requires m/z 298); $^1$H NMR (250 MHz, CDCl$_3$) δ 0.9 (6H, t&d, CH$_3$CH$_2$&CHCH$_3$), 1.27 (10H, m, CH$_3$(CH$_2$)$_5$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 7.64 (1H, d, NH).

Example 6

N-(3-Oxododecanoyl)-L-homoserine lactone (OdDHL)

$^1$H NMR (250 MHz, CDCl$_3$) δ 0.9 (3H, t, CH$_3$), 1.27 (12H, m, CH$_3$(CH$_2$)$_6$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 7.64 (1H, d, NH).

Example 7

N-(12-Bromo-3-oxododecanoyl)-L-homoserine lactone (12BrOdDHL)

$^1$H NMR (250 MHz, CDCl$_3$) δ 1.27 (10H, m, BrCH$_2$CH$_2$(CH$_2$)$_5$), 1.45 (2H, m, BrCH$_2$CH$_2$CH$_2$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 3.53 (2H, t, BrCH$_2$), 4.27 (1H, m, 5α-H), 4.48 (1H, td, 5β-H), 4.58 (1H, m, 3-H), 7.64 (1H, d, NH).

Example 8

N-(3-Oxotridecanoyl)-L-homoserine lactone (OtriDHL)

$^1$H NMR (250 MHz, CDCl$_3$) δ 0.9 (3H, t, CH$_3$), 1.27 (14H, m, CH$_3$(CH$_2$)$_7$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 7.64 (1H, d, NH).

Example 9

N-(13-Bromo-3-oxotridecanoyl)-L-homoserine lactone (13Br-OtriDHL)

ES-MS m/z 390.6 & 392.6 (MH+, C$_{17}$H$_{29}$NO$_4$Br requires m/z 390 & 392); $^1$H NMR (250 MHz, CDCl$_3$) δ 1.27 (12H, m, BrCH$_2$CH$_2$(CH$_2$)$_6$), 1.45 (2H, m, BrCH$_2$CH$_2$CH$_2$) 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 3.53 (2H, t, BrCH$_2$) 4.27 (1H, m, 5α-H), 4.48 (1H, td, 5β-H), 4.58 (1H, m, 3-H), 7.64 (1H, d, NH).

Example 10

N-(3-Oxo-12-tridecenoyl)-L-homoserine lactone (12dB-OtriDHL)

$^1$H NMR (250 MHz, CDCl$_3$) δ 1.27 (10H, m, CH$_2$CH(CH$_2$)$_5$), 1.59 (2H, m, CH$_2$CH$_2$CO), 2.00 (2H, m, CH$_2$CHCH$_2$) 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 4.93 (2H, m, CH$_2$CH), 5.86 (1H, m, CH$_2$CH), 7.64 (1H, d, NH).

Example 11

N-(3-Oxotetradecanoyl)-L-homoserine lactone (OtDHL)

$^1$H NMR (250 MHz, CDCl$_3$) δ 0.9 (3H, t, CH$_3$), 1.27 (16H, m, CH$_3$(CH$_2$)$_8$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 7.64 (1H, d, NH).

Example 12

N-(14-Bromo-3-oxotetradecanoyl)-L-homoserine lactone (14BrOtDHL)

$^1$H NMR (250 MHz, CDCl$_3$) δ 1.27 (14H, m, BrCH$_2$CH$_2$(CH$_2$)$_7$), 1.45 (2H, m, BrCH$_2$CH$_2$CH$_2$), 1.59 (2H, m, CH$_2$CH$_2$CO), 2.22 (1H, m, 4α-H), 2.52 (2H, t, CH$_2$CO), 2.76 (1H, m, 4β-H), 3.47 (2H, s, COCH$_2$CO), 3.53 (2H, t, BrCH$_2$), 4.27 (1H, m, 5α-H), 4.48 (1H, td, 5β-H), 4.58 (1H, m, 3-H), 7.64 (1H, d, NH).

Example 13

N-(13-Methoxycarbonyl-3-oxotridecanoyl)-L-homoserine lactone ((13MeO$_2$C)OtriDHL)

ES-MS m/z 370.3 (MH+, C$_{19}$H$_{32}$NO$_6$ requires m/z 370); $^1$H NMR (250 MHz, CDCl$_3$) δ 1.27 (10H, m, CH$_3$OCOCH$_2$CH$_2$(CH$_2$)$_5$), 1.59 (4H, m, CH$_2$CH$_2$CO & CH$_3$OCOCH$_2$CH$_2$), 2.22 (1H, m, 4α-H), 2.25 (2H, t, CH$_3$OCOCH$_2$), 2.52 (2H, t, CH$_2$CO), 2.76 (1H, m, 4β-H), 3.47 (2H, s, COCH$_2$CO), 3.58 (3H, s, CH$_3$O), 4.27 (1H, m, 5α-H), 4.48 (1H, td, 5β-H), 4.58 (1H, m, 3-H), 7.64 (1H, d, NH).

Example 14

N-(3-Oxo-7-tetradecenoyl)-L-homoserine lactone (7cis OtDHL)

$^1$H NMR (250 MHz, CDCl$_3$) δ 0.9 (3H, t, CH$_3$), 1.27 (8H, m, CH$_3$(CH$_2$)$_4$), 1.59 (2H, m, CH$_2$CH$_2$CO), 2.22 (1H, m, 4α-H), 1.95 (4H, m, CH$_2$CHCHCH$_2$), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 5.32 (2H, m, CHCH), 7.64 (1H, d, NH).

Example 15

N-(3-Oxo-9-tetradecenoyl)-L-homoserine lactone (9cis OtDHL)

ES-MS m/z 324.7 (MH+, C$_{18}$H$_{30}$NO$_4$ requires m/z 324); $^1$H NMR (250 MHz, CDCl$_3$) δ 0.9 (3H, t, CH$_3$), 1.27 (8H, m, CH$_3$(CH$_2$)$_2$ & (CH$_2$)$_2$CH$_2$CO), 1.59 (2H, m, CH$_2$CH$_2$CO), 2.22 (1H, m, 4α-H), 1.95 (4H, m, CH$_2$CHCHCH$_2$), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 5.32 (2H, m, CHCH), 7.64 (1H, d, NH).

Example 16

N-(3-Oxo-10-tetradecenoyl)-L-homoserine lactone (10cis OtDHL)

ES-MS m/z 323.8 (MH+, C$_{18}$H$_{30}$NO$_4$ requires m/z 324); $^1$H NMR (250 MHz, CDCl$_3$) δ 0.9 (3H, t, CH$_3$), 1.27 (8H, m, CH$_3$CH$_2$ & (CH$_2$)$_3$CH$_2$CO), 1.59 (2H, m, CH$_2$CH$_2$CO), 2.22 (1H, m, 4α-H), 1.95 (4H, m, CH$_2$CHCHCH$_2$), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 5.32 (2H, m, CHCH), 7.64 (1H, d, NH).

Example 17

N-(3-Oxo-11-tetradecenoyl)-L-homoserine lactone (11cis OtDHL)

ES-MS m/z 324.3 (MH+, C$_{18}$H$_{30}$NO$_4$ requires m/z 324); $^1$H NMR (250 MHz, CDCl$_3$) δ 0.9 (3H, t, CH$_3$), 1.27 (8H, m, (CH$_2$)$_4$CH$_2$CO), 1.59 (2H, m, CH$_2$CH$_2$CO), 2.22 (1H, m, 4α-H), 1.95 (4H, m, CH$_2$CHCHCH$_2$), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 5.32 (2H, m, CHCH), 7.64 (1H, d, NH).

Example 18

N-(3-Oxo-13-tetradecenoyl)-L-lactone homoserine (13dbOtDHL)

ES-MS m/z 323.6 (MH+, C$_{18}$H$_{30}$NO$_4$ requires m/z 324); $^1$H NMR (250 MHz, CDCl$_3$) δ 1.27 (12H, m, CH$_2$CH (CH$_2$)$_6$), 1.59 (2H, m, CH$_2$CH$_2$CO), 2.00 (2H, m, CH$_2$CHCH$_2$), 2.22 (1H, m, 4α-H), 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 4.93 (2H, m, CH$_2$CH), 5.86 (1H, m, CH$_2$CH), 7.64 (1H, d, NH).

Example 19

N-(12-Hydroxy-3-oxododecanoyl)-L-homoserine lactone (12OHOdDHL)

Using 10-acetoxydecanoic acid in the general procedure as described above in Example 1 afforded the N-(12-acetoxy-3-oxododecanoyl)-L-homoserine lactone. The latter when refluxed in 1M hydrochloric acid, yielded the title product.

$^1$H NMR (250 MHz, CDCl$_3$) δ 1.27 (12H, m, HOCH$_2$ (CH$_2$)$_6$), 1.59 (2H, m, CH$_2$CH$_2$CO), 1.89 (1H, t, OH), 2.22 (1H, m, 4α-H), 2.52 (2H, t, CH$_2$CO), 2.76 (1H, m, 4β-H), 3.47 (2H, s, COCH$_2$CO), 3.60 (2H, t, HOCH$_2$), 4.27 (1H, m, 5α-H), 4.48 (1H, td, 5β-H), 4.58 (1H, m, 3-H), 7.64 (1H, d, NH).

Example 20

N-[11-(N,N-Dimethylcarbamoyl)-3-oxoundecanoyl]-L-homoserine lactone (11Me$_2$NCO)OuDHL)

9-(N,N-Dimethylcarbamoyl)nonanoic acid was prepared as follows:

To a solution of the decandioic acid mono methyl ester (2 mmol) in dry tetrahydrofuran (20 ml) was added 1-hydroxybenzotriazole (1 mmol), N,N'-dicyclohexylcarbodiimide (1.1 mmol) and N,N-dimethylamine (2M solution in tetrahydrofuran, 2 ml). The mixture was stirred overnight and then filtered. The solvent was removed in vacuo and the residue redissolved in ethyl acetate. The ethyl acetate solution was washed sequentially with saturated sodium hydrogen carbonate solution, 1M potassium hydrogen sulphate solution and saturated sodium chloride solution. After drying over anhydrous magnesium sulphate and removal of the solvent, the product was purified by preparative layer chromatography on silica plates in ethyl acetate to afford methyl 9-(N,N-dimethylcarbamoyl)nonanoate.

The methyl ester was stirred in 1M sodium hydroxide (20 ml) and methanol (10 ml) solution overnight. The methanol was removed in vacuo and the solution acidified to pH 1 with 2M hydrochloric acid. The product was extracted with dichloromethane (3×10 ml) and the combined extracts were dried over anhydrous magnesium sulphate and concentrated by rotary evaporation to give the desired 9-(N,N-dimethylcarbamoyl)nonanoic acid.

$^1$H NMR (250 MHz, CDCl$_3$) δ 1.27 (8H, m, NCOCH$_2$CH$_2$CH$_2$(CH$_2$)$_4$), 1.59 (4H, m, CH$_2$CH$_2$CO&NCOCH$_2$CH$_2$), 2.22 (1H, m, 4α-H), 2.40 (2H, t, NCOCH$_2$ 2.52 (2H, t, CH$_2$CO), 2.76 (1H, m, 4β-H), 3.47 (2H, s, COCH$_2$CO), 4.27 (1H, m, 5α-H), 4.48 (1H, td, 5β-H), 4.58 (1H, m, 3-H), 7.64 (1H, d, NH).

Example 21

N-(3-Hydroxydodecanoyl)-L-homoserine lactone (HdDHL)

N-(3-Oxododecanoyl)-L-homoserine lactone (1 mmol) was dissolved in methanol (10 ml) and the solution made acidic (pH 3~4) with 2 M HCl-methanol. Sodium cyanoborohydride (2.5 mmol) was added in one lot with stirring and the reaction mixture maintained at pH 3~4 by the occasional addition of 2 M HCl-methanol. After 2 hours, solvent was removed in vacuo and ethyl acetate extracts (3×10 ml) of the residue were combined, dried (MgSO$_4$) and evaporated to yield the title hydroxy derivatives. The products were purified by preparative layer chromatography on silica plates in CHCl$_3$—MeOH (9:1).

$^1$H NMR (250 MHz, CDCl$_3$) δ 0.87 (3H, t, CH$_3$), 1.27 (14H, m, (CH$_2$)CH$_2$CHOH), 1.56 (2H, m, CH$_2$CHOH), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 7.64 (1H, d, NH).

Other N-(3-hydroxyacylated)-L-homoserine lactones were prepared according to the procedure described above in Example 21 by reducing the appropriate -3-oxo compound as follows.

Example 22

N-(3-Hydroxytetradecanoyl)-L-homoserine lactone (HtDHL)

ES-MS m/z 328.1 (MH+, C$_{18}$H$_{34}$NO$_4$ requires m/z 328); $^1$H NMR (250 MHz, CDCl$_3$) δ 0.87 (3H, t, CH$_3$), 1.27 (18H, m, (CH$_2$)$_9$CH$_2$CHOH), 1.56 (2H, m, CH$_2$CHOH), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 7.64 (1H, d, NH).

Example 23

N-(3-Hydroxy-7-tetradecenoyl)-L-homoserine lactone (7cis HtDHL)

$^1$H NMR (250 MHz, CDCl$_3$) δ 0.9 (3H, t, CH$_3$), 1.27 (10H, m, CH$_3$(CH$_2$)$_4$ & CH$_2$CH$_2$CHOH), 1.40 (2H, m, CH$_2$CHOH), 2.00 (4H, m, CH$_2$CHCHCH$_2$), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 5.32 (2H, m, CHCH), 7.64 (1H, d, NH).

Example 24

N-(3-Hydroxy-9-tetradecenoyl)-L-homoserine lactone (9cis HtDHL)

ES-MS m/z 326.3 (MH+, C$_{18}$H$_{32}$NO$_4$ requires m/z 326); $^1$H NMR (250 MHz, CDCl$_3$) δ 0.9 (3H, t, CH$_3$), 1.27 (10H, m, CH$_3$(CH$_2$)$_2$ & (CH$_2$)$_3$CH$_2$CHOH), 1.40 (2H, m, CH$_2$CHOH), 2.00 (4H, m, CH$_2$CHCHCH$_2$), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 5.32 (2H, m, CHCH), 7.64 (1H, d, NH).

Example 25

N-(3-Hydroxy-10-tetradecenoyl)-L-homoserine lactone (10cis HtDHL)

ES-MS m/z 325.6 (MH+, $C_{18}H_{32}NO_4$ requires m/z 326); $^1$H NMR (250 MHz, CDCl$_3$) δ 0.9 (3H, t, CH$_3$), 1.27 (10H, m, CH$_3$CH$_2$ & (CH$_2$)$_4$CH$_2$CHOH), 1.40 (2H, m, CH$_2$CHOH), 2.00 (4H, m, CH$_2$CHCHCH$_2$), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 5.32 (2H, m, CHCH), 7.64 (1H, d, NH).

Example 26

N-(3-Hydroxy-11-tetradecenoyl)-L-homoserine lactone (11cis HtDHL)

ES-MS m/z 325.7 (MH$^+$, $C_{18}H_{32}NO_4$ requires m/z 326); $^1$H NMR (250 MHz, CDCl$_3$) δ 0.9 (3H, t, CH$_3$), 1.27 (10H, m, (CH$_2$)$_5$CH$_2$CHOH), 1.40 (2H, m, CH$_2$CHOH), 2.00 (4H, m, CH$_2$CHCHCH$_2$), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 5.32 (2H, m, CHCH), 7.64 (1H, d, NH).

Example 27

N-(3-Hydroxy-13-tetradecenoyl)-L-homoserine lactone (13dbHtDHL)

ES-MS m/z 326.3 (MH+, $C_{18}H_{32}NO_4$ requires m/z 326); $^1$H NMR (250 MHz, CDCl$_3$) δ 1.27 (14H, m, (CH$_2$)$_7$CH$_2$CHOH), 1.40 (2H, m, CH$_2$CHOH), 2.00 (2H, m, CH$_2$CHCH$_2$), 2.22 (1H, m, 4α-H), 2.38 (2H, m, CHOHCH$_2$CO), 2.76 (1H, m, 4β-H), 3.15 (1H, m, CHOH), 3.98 (1H, brs, OH), 4.27 (1H, m, 5α-H), 4.48 (1H, td, 5β-H), 4.58 (1H, m, 3-H), 5.32 (2H, m, CHHCH, 5.83 (1H, m, CHHCH), 7.64 (1H, d, NH).

Example 28

Synthesis of 2-heptyl-3-hydroxy-4(1H)-quinolone

Preparation of 5-octanoyl Meldrum's Acid (2,2-dimethyl-5-octanoyl-1,3-dioxane-4,6-dione)

N,N'-Dicyclohexylcarbodiimide (11 mmol) was added to a stirred solution of octanoic acid (10 mmol) and 4-dimethylaminopyridine (12 mmol) in dry dichloromethane (40 ml). The mixture was stirred at room temperature for 1 hour and Meldrum's acid (10 mmol) was added. The stirring was continued at room temperature overnight. The solvent was removed in vacuum and the residue redissolved in ethyl acetate and filtered. The filtrate was washed with 2 M HCl solution and dried over MgSO$_4$. The solvent was rotary evaporated to obtain the title product as an oil in 95% yield and was used without purification in the next step.

Preparation of ethyl 3-oxodecanoate

A solution of 5-octanoyl Meldrum's acid (10 mmol) in dry ethanol (50 ml) was heated under reflux for 4 hours. The solvent was evaporated in vacuum and the residue redissolved in ethyl acetate. The solution was sequentially washed with a saturated solution of sodium bicarbonate, 1 M KHSO$_4$ and finally brine. Drying (MgSO$_4$) and concentration in vacuum afforded the title β-keto ester as an oil in nearly quantitative yield.

$^1$H NMR (90 MHz, CDCl$_3$) δ 0.9 (3H, t, CH$_3$), 1.3 (11H, m, OCH$_2$CH$_3$ and CH$_3$(CH$_2$)$_4$), 1.6 (2H, m, CH$_2$CH$_2$CO), 2.5 (2H, t, CH$_2$CO), 3.4 (2H, s, COCH$_2$CO), 4.2 (3H, q, OCH$_2$).

Preparation of ethyl 3-anilino-2-decenoate

A solution of aniline (6 mmol), ethyl 3-oxodecanoate (6 mmol) and toluene-p-sulfonic acid (50 mg) in dry toluene (60 ml) was heated under reflux for 24 hours using Dean-Stark apparatus for the azeotropic removal of water. The solvent was removed in vacuum to afford the title product as an oil which was used without purification in the next step.

Preparation of 2-heptyl-4(1H)-quinolone

The crude product of ethyl 3-anilino-2-decenoate was mixed with diphenyl ether (50 ml) and heated under reflux for 30 minutes. The solution was cooled to room temperature and then diluted with petroleum ether (b.p. 60-80° C.; 200 ml). The mixture was stirred and the petroleum ether decanted off. The product was chromatographed on a silica column using 3% MeOH/CH$_2$Cl$_2$ as the mobile phase. 2-Heptyl-4(1H)-quinolone was obtained as a crystalline solid in 50% yield.

$^1$H NMR (90 MHz, CDCl$_3$) δ 0.8 (3H, t, CH$_3$), 1.2 (8H, m, CH$_3$(CH$_2$)$_4$), 1.7 (2H, m, NHCCH$_2$CH$_2$), 2.7 (2H, m, NHCCH$_2$), 6.2 (1H, s, 3-H), 7.3 (1H, m, 6-H), 7.6 (1H, m, 7-H), 7.8 (1H, d, 5-H), 8.4 (1H, d, 8-H), 12.7 (1H, br s, NH).

Preparation of 3-formyl-2-heptyl-4(1H)-quinolone

A mixture of 2-heptyl-4(1H)-quinolone (5 mmol), hexamine (2.5 mmol), and TFA (7.5 ml) was stirred at reflux under nitrogen for 30 hours. MeOH (15 ml) and water (15 ml) were added, and heating was continued for 1 hour. 3 M HCl (5 ml) was added and the heating was continued for a further period of 30 minutes. The mixture was cooled and the precipitate removed by filtration and washed with water. The solid on trituration with acetone afforded the title compound in 40% yield. Recrystallisation from MeOH/EtOAc gave colourless needles, mp 245-248° C. (dec).

$^1$H NMR (250 MHz, DMSO-d$_6$) δ 0.82 (3H, t, CH$_3$), 1.27 (8H, m, CH$_3$(CH$_2$)$_4$), 1.6 (2H, m, NHCCH$_2$CH$_2$), 3.0 (2H, m, NHCCH$_2$), 7.38 (1H, dd, 6-H), 7.57 (1H, d, 7-H), 7.70 (1H, dd, 5-H), 8.12 (1H, d, 8-H), 10.37 (1H, s, CHO), 12.12 (1H, brs, NH).

Preparation of 2-heptyl-3-hydroxy-4(1H)-quinolone

Aqueous hydrogen peroxide (27.5 wt % solution in water, 145 μl) was added to a solution of 3-formyl-2-heptyl-4(1H)-quinolone (1 mmol) in EtOH (3 ml) and 1M NaOH solution (1.0 ml) under nitrogen, and the mixture was stirred at room temperature for 6 hours. The precipitate was removed by filtration, air dried and crystallised from EtOAc to give 2-heptyl-3-hydroxy-4(1M-quinolone in 70% yield as off-white needles, mp 195-197° C.

$^1$H NMR (250 MHz, DMSO-d$_6$) δ 0.82 (3H, t, CH$_3$), 1.27 (8H, m, CH$_3$(CH$_2$)$_4$), 1.63 (2H, m, NHCCH$_2$CH$_2$), 2.72 (2H, m, NHCCH$_2$), 7.20 (1H, m, 6,7-H$_2$), 7.52 (2H, m, 5-H), 8.00 (1H, br s, OH), 8.08 (1H, d, 8-H), 11.44 (1H, br s, NH).

EXPERIMENTAL

I. Immunomodulatory Activity of Homoserine Lactone Compounds Materials and Methods

I.I ConA Mitogen-Stimulated Proliferation of Murine Splenocytes

The concanavalin A (ConA) cell proliferation assay was used to assess the effect of homoserine lactone (HSL) compounds on T-cell activation and proliferation. Proliferation was assessed by the incorporation of [$^3$H]-thymidine into DNA. Eight-week-old female BALB/c mice were obtained from Harlan (Bicester, Oxon, UK) and given food and water ad libitum. Splenocyte suspensions were prepared by removing the spleens and placing them into RPMI 1640 medium. The spleens were forced through 70-µm-pore-size wire gauzes using the plunger from a 5-ml syringe to produce a single cell suspension. The cells were pelleted by centrifugation, and erythrocytes were lysed with 0.017 M Tris, 0.144 M ammonium chloride buffer, pH 7.2. Leucocytes were washed twice with RPMI 1640 medium with 2% (vol/vol) foetal calf serum (FCS) and resuspended in complete cell culture medium (CTCM) consisting of RPMI 1640 medium with 5% FCS, 2 mM L-glutamine, and $5\times10^{-5}$ M 2-mercaptoethanol. HSL compounds were tested at doubling down dilutions ranging from 1 mM to 0.1 µM in a final volume of 200 µl of CTCM, containing ConA (Sigma, Poole, UK) at 1 µg/ml and 100,000 spleen cells. Following incubation for 48 h at 37° C. in 5% $CO_2$-air, 0.25 µCi [$^3$H]-thymidine (Amersham) in 10 µl volume made up in RPMI 1640 medium was added and the cells were incubated for a further 24 h. Cells were harvested onto fibreglass filters with a Packard filtermate harvester. After the addition of 25 µl of MicroScint-O (Packard) to each well the filters were counted with the Packard TopCount scintillation counter.

Figure 1:
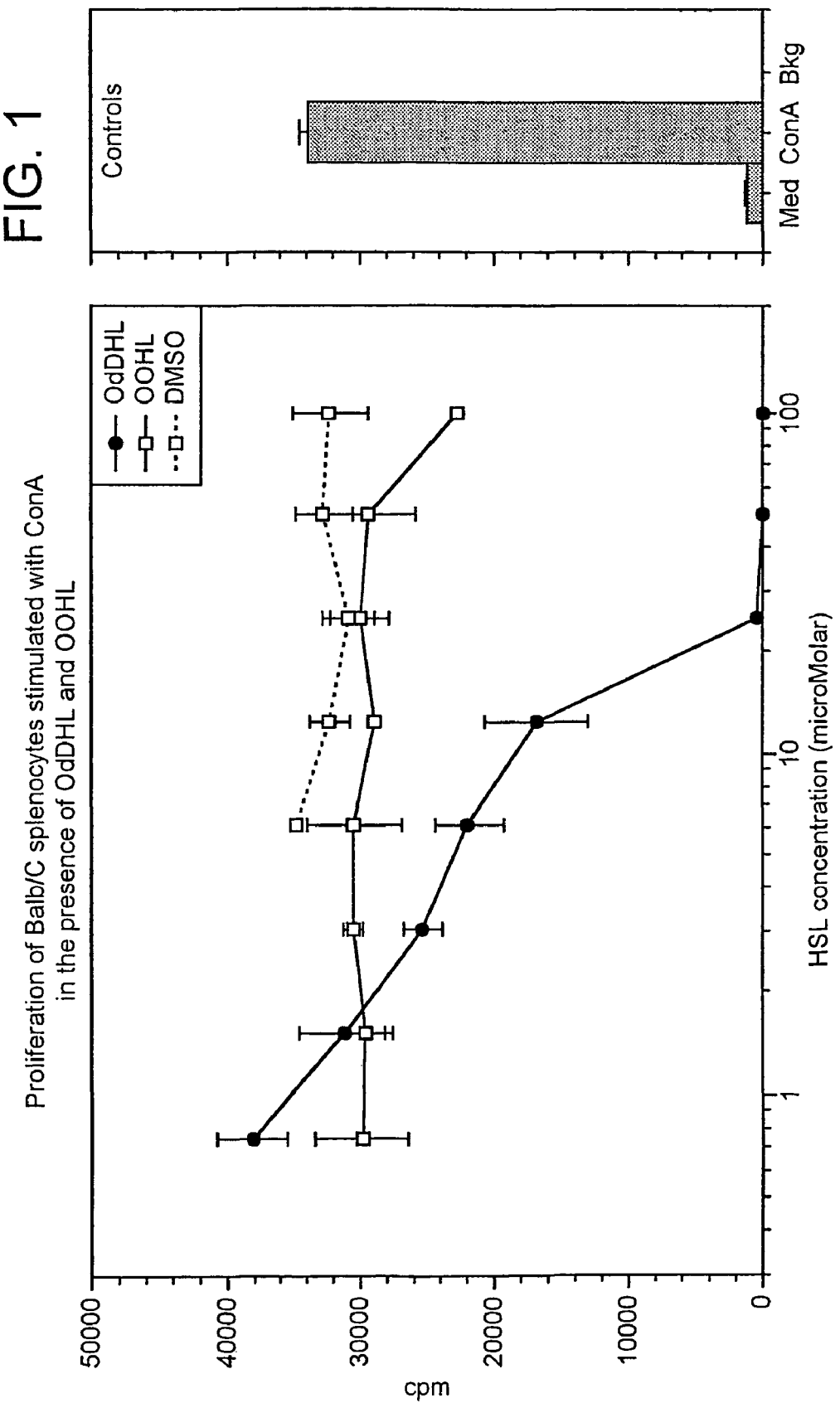
FIG. 1 shows the inhibitory effect on murine splenocyte proliferation as indicated by the plots of counts per minute (cpm) against the concentrations (micromolar) of the HSL compounds N-(3-oxododecanoyl)-L-homoserine lactone (OdDHL) and N-(3-oxooctanoyi)-L-homoserine lactone (OOHL) and the vehicle dimethylsulphoxide (DMSO).

Mitogen (Concanavalin A) induced murine splenocyte proliferation was indicated by the incorporation of tritated thymidine into the DNA in the mouse spleen cells as shown by counts per minute using the scintillation counter. The inhibitory effect of an HSL compound being tested on cell proliferation was indicated by a reduction in counts per minute. FIG. 1 shows the plots of counts per minute (cpm) against the concentrations (micromolar) of the HSL compounds N-(3-oxododecanoyl)-L-homoserine lactone (OdDHL) and N-(3-oxooctanoyl)-L-homoserine lactone (OOHL) and the vehicle dimethylsulphoxide (DMSO). It can be seen, from this figure, that OdDHL inhibits splenocyte proliferation. In contrast, OOHL and DMSO failed to inhibit proliferation.

The IC50 value, i.e., the concentration (micromolar) of a compound which inhibits cell proliferation thymidine incorporation by 50% was determined for several compounds of the present invention and these IC 50 values are shown in column A of the Table below.

I.II ConA Mitogen-Stimulated Proliferation of Human PBMC

Blood specimens were obtained with consent from healthy human volunteers. Human peripheral blood mononuclear cells (PBMC) were isolated from heparinised whole blood by buoyant density centrifugation over Histopaque 1077 (Sigma, Poole, UK) at 600 g for 20 minutes. PBMC harvested from the 'buffy' layers were washed twice with RPMI 1640 medium and resuspended in CTCM. HSL compounds were tested at similar dilutions as for murine splenocytes in 200 µl of CTCM, containing 1 µg/ml of ConA and 100,000 PBMC. Human PBMC were incubated for 48 h at 37° C. in 5% $CO_2$-air, followed by pulsing with 0.25 µCi [$^3$H]-thymidine (see above). After a further incubation of 24 h cells were harvested onto fibreglass filters and then counted in the presence of MicroScint-O with the Packard TopCount.

Figure 2:
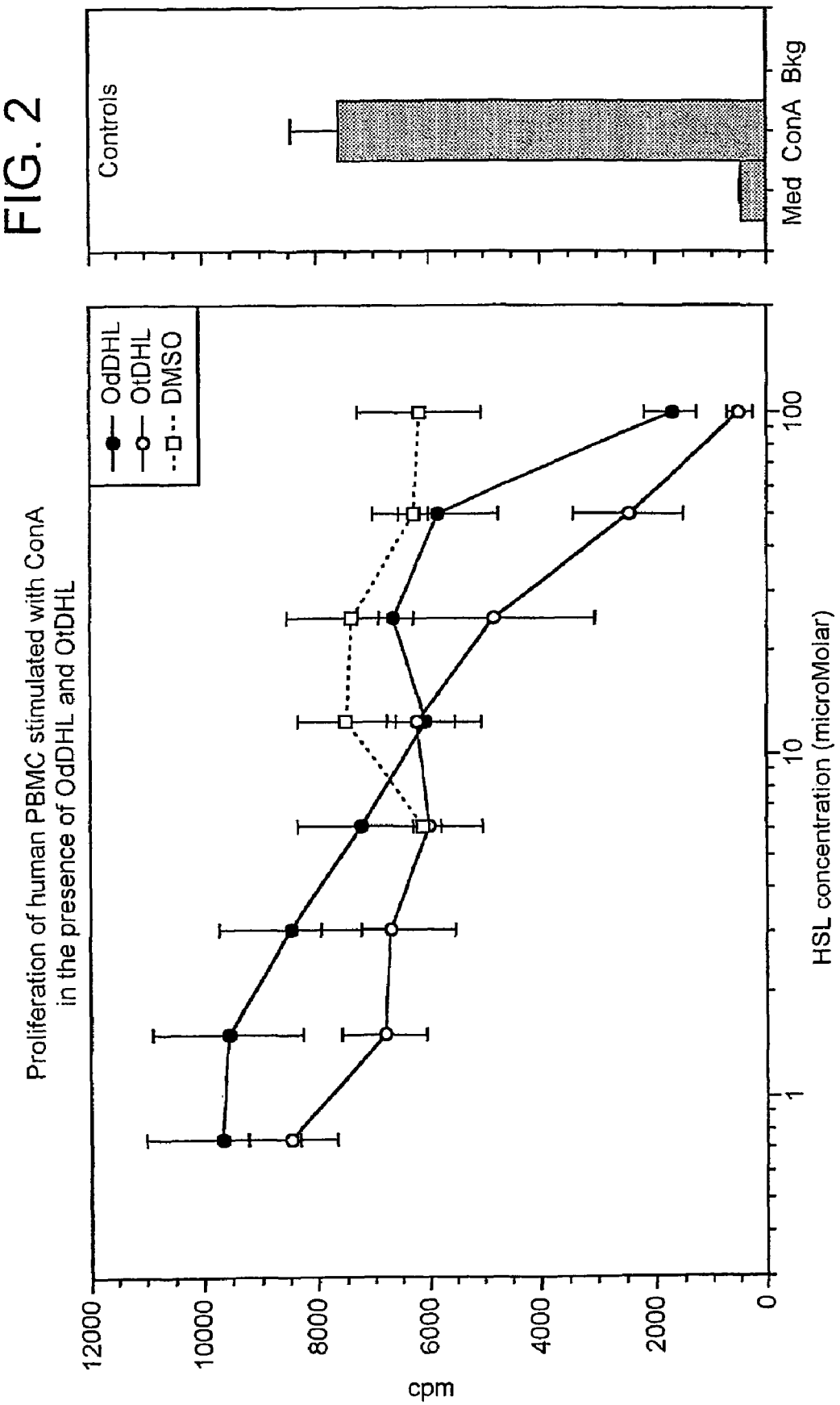
FIG. 2 shows the inhibitory effect on human peripheral blood mononuclear cells (PBMC) as indicated by the plots of counts per minute (cpm) against the concentrations (micromolar) of the HSL compounds N-(3-oxododecanoyl)-L-homoserine lactone (OdDHL) and N-(3-oxooctanoyl)-L-homoserine lactone (OOHL) and the vehicle dimethylsulphoxide (DMSO).

Concanavalin induced cell proliferation of human peripheral blood mononuclear cells (PBMC) was tracked, as described in I above, by a measurement of counts per minute using the scintillation counter. The inhibitory effect of an HSL compound being tested on cell proliferation was indicated by a reduction in counts per minute. FIG. 2 shows the plots of cpm against the concentrations of OdDHL, N-(3-oxotetradecanoyl)-L-homoserine lactone (OtDHL) and DMSO (vehicle). As can be seen, both OdDHL and OtDHL inhibited proliferation of human PBMC stimulated with Concanavalin A. The IC50 values for several HSL compounds of the invention were determined and these are shown in columns B, C and D in the Table below. Columns B, C and D represent different sources of human PBMC samples used.

I.III TNF-alpha Production from LPS-Stimulated Human PBMC

Bacterial lipopolysaccharide (LPS) stimulates the production of a variety of cytokines, including TNF-alpha, from human PBMC; these cytokines in turn influence the development of T cells, supporting a T helper 1 conducive milieu. Human PBMC prepared from whole blood by buoyant density centrifugation were resuspended in CTCM. HSL compounds were again tested at similar dilutions as for murine splenocytes in 200 µl of CTCM, containing $5\times10^{-5}$ µg/ml LPS *Escherichia coli* strain 055:B5 (Sigma, Poole, UK) and 100,000 PBMC. Following incubation for 24 h at 37° C. in 5% $CO_2$-air, the cell culture supernatants were collected and tested for TNF-alpha levels by 'sandwich' ELISA. Briefly, 96-well Nunc MaxiSorp (Life Technologies, Paisley, UK) plates were coated with 50 µl of a 2 µg/ml solution of mouse anti-human TNF-alpha monoclonal antibody (Pharmingen, UK) in 0.05 M carbonate/bicarbonate buffer, pH 9.6 overnight at 4° C. After washing the plates three times with PBS-Tween, which contained phosphate buffered saline (PBS) with 0.5% (vol/vol) Tween 20 (Sigma, Poole, UK), the plates were blocked with 1% (wt/vol) bovine serum albumin (BSA) (Sigma, Poole, UK) at room temperature for 2 h. Following three washes with PBS-Tween, 50 µl of cell culture supernatants were added and incubated overnight at 4° C.; standard human TNF-alpha (Pharmingen, UK) ranging from 2000 to 31.25 pg/ml were included for each plate. After four washes with PBS-Tween, 50 µl of a second antibody, biotinylated mouse anti-human TNF-alpha monoclonal antibody (Pharmingen, UK) was added at 0.5 µg/1 ml diluted in 1% BSA in PBS-Tween and incubated at room temperature for 1 h. Following four washes, the bound biotinylated antibody was detected with 50 µl of a 1:1,000 dilution of Streptavidin-peroxidase (Pharmingen, UK). At the end of an hour incubation at room temperature, the plates were thoroughly washed six times with PBS-Tween and the assay was developed by the addition of 100 µl of 0.1 mg/ml of tetramethyl benzidine subtrate (Sigma, Poole, UK) in 0.1 M sodium acetate buffer, pH 6 containing 0.03% $H_2O_2$. The enzyme reaction was stopped with 50 µl of 2.5 M $H_2SO_4$ after an incubation of 10 minutes at room temperature and the development was read at 450 nm with a spectrophotometric 96-well plate reader (Dynex).

Figure 3:
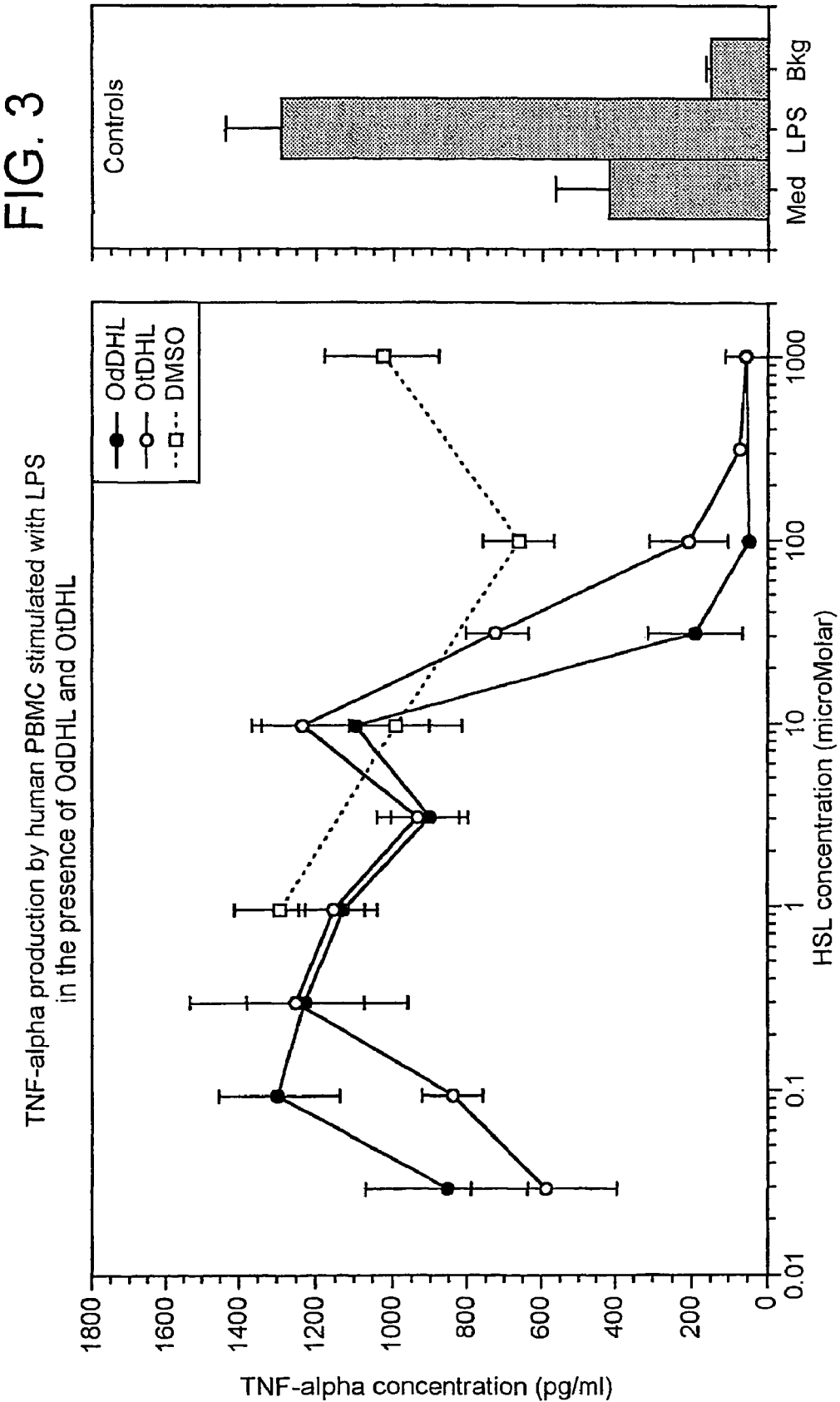
FIG. 3 shows the effect of the of the concentration on lipopolysaccharide (LPS) induced TNF-αproduction by human peripheral blood mononuclear cells (PBMC) as indicated by plots of TNF-α concentrations (pg/ml) against the concentration (micromolar) of N-(3-oxododecanoyl)-L-homoserine lactone (OdDHL). N-(3-oxotetradecanoyl)-L-homoserine lactone (OtDHL) and DMSO (vehicle).

The effect of the concentration of certain HSL compounds of the invention on LPS induced TNF-α production by human PBMC was observed. FIG. 3 shows plots of TNF-α concentrations (pg/ml) against the concentration (micromolar) of OdDHL, OtDHL and DMSO (vehicle). As can be seen, both OdDHL and OtDHL inhibited the secretion of the T helper 1-supporting cytokine TNF-α. The IC50 values, i.e., the concentration (micromolar) of a compound which inhibits TNF-α secretion by 50%, was determined for some of the HSL compounds of the invention and these are shown in column E in the Table below.

Similar studies were carried out using, as the HSL compounds, N-(12-bromo-3-oxododecanoyl)-L-homoserine lactone (12BrOdDHL) and N-(12-hydroxy-3-oxododecanoyl)-L-homoserine lactone (12hydroxyOdDHL) and the plots for these are shown in FIG. 4. For comparison purposes, similar studies were carried out using, as the HSL, the known shorter side chain compound N-(3-oxohexanoyl)-L-homoserine lactone (OHHL) and the plot for this is shown in FIG. 5. The difference in activity between OHHL and OdDHL is marked. Also for comparison purposes, similar studies were carried out using the known drugs dexamethasone and Cyclosporin A (CsA) and the plots for these are shown in FIG. 6. The IC50 value for dexamethasone was determined to be 500.

I.IV Optimisation of Cell Culture Conditions

In the cell culture assays the number of cells used (mouse splenocytes and human PBMC) was initially optimised to 100,000 cells per well. The optimal dose of ConA of 1 µg/ml used in the cell proliferation assays was determined from ConA titration curves. A similar titration curve was established for LPS stimulation to obtain an LPS concentration which stimulated a suboptimal level of TNF-alpha release from human PBMC.

II. Immunomodulatory Activity of 2-heptyl-3-hydroxy-4(1H)-quinolone Materials and Methods II.I ConA Mitogen-Stimulated Proliferation of Murine Splenocytes The concanavalin A (ConA) cell proliferation assay was used to assess the effect of the title compound on T-cell activation and proliferation. Proliferation was assessed by the incorporation of [$^3$H]-thymidine into DNA. Eight-week-old female BALB/c mice were obtained from Harlan (Bicester, Oxon, UK) and given food and water ad libitum. Splenocyte suspensions were prepared by removing the spleens and placing them into RPMI 1640 medium. The spleens were forced through 70 µm pore size wire gauzes using the plunger from a 5 ml syringe to produce a single cell suspension. The cells were pelleted by centrifugation, and erythrocytes were lysed with 0.017 M Tris, 0.144 M ammonium chloride buffer, pH 7.2. Leucocytes were washed twice with RPMI 1640 medium with 2% (vol/vol) foetal calf serum (FCS) and resuspended in complete cell culture medium (CTCM) consisting of RPMI 1640 medium with 5% FCS, 2 mM L-glutamine, and 5×10$^{-5}$ M 2-mercaptoethanol. The title compound was tested at doubling down dilutions containing ConA (Sigma, Poole, UK) at 1 g/ml and 100,000 spleen cells. Following incubation for 48 h at 37° C. in 5% COrair, 0.25 µCi [$^3$H]-thymidine (Amersham) in 10 µl volume made up in RPMI 1640 medium was added and the cells were incubated for a further 24 h. Cells were harvested onto fibreglass filters with a Packard filtermate harvester. After the addition of 25 µl of MicroScint-O (Packard) to each well the filters were counted with the Packard Top-Count scintillation counter.

| EX NO. | COMPOUND TESTED | NAME ABBREVIATION | A | B | C | D | E |
|---|---|---|---|---|---|---|---|
| 1 | N-(3-Oxoundecanoyl)-L-homoserine lactone | OuDHL | 9 | 63 | 13 | 44 | |
| 2 | N-(11-Bromo-3-oxoundecanoyl)-L-homoserine lactone | 11BrOuDHL | 6 | 18 | | | |
| 3 | N-(10-Methyl-3-oxoundecanoyl)-L-homoserine lactone | 10MeOuDHL | 8 | | | 25 | |
| 4 | N-(10-Methoxycarbonyl-3-oxodecanoyl)-L-homoserine lactone | 10(MeO$_2$C)ODHL | 73 | 20 | | 63 | |
| 5 | N-(6-Methyl-3-oxoundecanoyl)-L-homoserine lactone | 6MeOuDHL | 5 | 20 | | | |
| 6 | N-(3-Oxododecanoyl)-L-homoserine lactone | OdDHL | 4 | 60 | 7 | 34 | 17 |
| 7 | N-(12-Bromo-3-oxododecanoyl)-L-homoserine lactone | 12BrOdDHL | 6 | 20 | | 7 | 63 |
| 8 | N-(3-Oxotridecanoyl)-L-homoserine lactone | OtriDHL | 4 | 41 | 7 | 25 | |
| 9 | N-(13-Bromo-3-oxotridecanoyl)-L-homoserine lactone | 13BrOtriDHL | 3 | 8 | | 12 | |
| 10 | N-(3-Oxo-12-tridecenoyl)-L-homoserine lactone | 12dbOtriDHL | 7 | | | | |
| 11 | N-(3-Oxotetradecanoyl)-L-homoserine lactone | OtDHL | 6 | 32 | 12 | 30 | 35 |
| 12 | N-(14-Bromo-3-oxotetradecanoyl)-L-homoserine lactone | 14BrOtDHL | 8 | | | | |
| 13 | N-(13-Methoxycarbonyl-3-oxotridecanoyl)-L-homoserine lactone | 13(MeO$_2$C)OtriDHL | 6 | 15 | | 20 | |
| 14 | N-(3-Oxo-7-tetradecenoyl)-L-homoserine lactone | 7cisOtDHL | 17 | | | | |
| 15 | N-(3-Oxo-9-tetradecenoyl)-L-homoserine lactone | 9cisOtDHL | | | | | |
| 16 | N-(3-Oxo-10-tetradecenoyl)-L-homoserine lactone | 10cisOtDHL | 15 | | | | |
| 17 | N-(3-Oxo-11-tetradecenoyl)-L-homoserine lactone | 11cisOtDHL | 12 | | | | |
| 18 | N-(3-Oxo-13-tetradecenoyl)-L-homoserine lactone | 13dbOtDHL | 10 | | | | |
| 19 | N-(12-Hydroxy-3-oxododecanoyl)-L-homoserine lactone | 12hydroxyOdDHL | 9 | | | | 70 |
| 20 | N-[11-(N,N-Dimethylcarbamoyl)-3-oxoundecanoyl]-L-homoserine lactone | 11(Me$_2$NCO)OuDHL | 35 | | | | |
| 21 | N-(3-Hydroxydodecanoyl)-L-homoserine lactone | HdDHL | 12 | | | | |
| 22 | N-(3-Hydroxytetradecanoyl)-L-homoserine lactone | HtDHL | 7 | | | | |
| 23 | N-(3-Hydroxy-7-tetradecenoyl)-L-homoserine lactone | 7cisHtDHL | 12 | | | | |
| 24 | N-(3-Hydroxy-9-tetradecenoyl)-L-homoserine lactone | 9cisHtDHL | 15 | | | | |
| 25 | N-(3-Hydroxy-10-tetradecenoyl)-L-homoserine lactone | 10cisHtDHL | 20 | | | | |
| 26 | N-(3-Hydroxy-11-tetradecenoyl)-L-homoserine lactone | 11cisHtDHL | 20 | | | | |
| 27 | N-(3-Hydroxy-13-tetradecenoyl)-L-homoserine lactone | 13cisHtDHL | 18 | | | | |

Notes to Table
Column A shows IC50 values (µM) for compounds in inhibition of ConA induced murine splenocyte proliferation (Experiment I)
Columns B, C & D show, for different sources of human PBMC, IC50 values (µM) for compounds in inhibition of ConA induced cell proliferation of PBMC (Experiment II)
Column E shows IC5O values (µM) for compounds in inhibition of LPS induced production of TNF-α by human PBMC (Experiment III)

Mitogen (Concanavalin A) induced murine splenocyte proliferation was indicated by the incorporation of tritated thymidine into the DNA in the mouse spleen cells as shown by counts per minute using the scintillation counter. The inhibitory effect of the title compound being tested on cell proliferation was indicated by a reduction in counts per minute. FIG. 7 shows the plots of counts per minute (cpm) against the concentrations (micromolar) of the title compound and the vehicle dimethylsulphoxide (DMSO). It can be seen, from this figure, that 2-heptyl-3-hydroxy-4(1H) quinolone inhibits splenocyte proliferation.

II.II According to our experiments, both OdDHL and 2-n-heptyl-3-hydroxy-4(1H quinolone (PQS) inhibit the proliferation of BALB/c splenocytes stimulated with 1 µg/ml Con A (FIGS. 1 and 7) and also inhibit the release of IL-2 from BALB/c splenocytes (FIG. 12). However, whereas the release of TNF-α from human PBMC stimulated with LPS is inhibited by OdDHL (FIG. 3) it is not inhibited by PQS (FIG. 13).

III Immunomodulatory Activity of a Combination of N-(3-oxododecanoyl) Homoserine Lactose (OdDHL) and 2-heptyl-3-hydroxy-4(1H)-quinolone (PQS)

III.I A concanavalin A (Con A) cell proliferation assay was used to assess the effect of a combination of OdDHL and PQS on T-cell activation and proliferation in accordance with the procedure set out in 1.1 above.

In this, the effect of an inactive amount of OdDHL alone (6.25 µM) was compared with that achieved for PQS alone (at concentrations in the range of from 0.125 to 4 µM) and with 6.25 µM OdDHL in the presence of PQS (at concentrations of from 0.125 to 4 µM). The results (shown in FIG. 8) indicate that a synergistic inhibition of proliferation is achieved using an amount of OdDHL (which amount is inactive when the OdDHL is present on its own) together with an amount of PQS. The proliferation of Balb/C splenocytes stimulated with 1 µg/ml Con A was also investigated according to the procedure set out in II.I in the presence of various concentrations of different quorum sensing molecules (PQS, OdDHL and OHHL) and, as a control, the vehicle DMSO on its own. A plot of counts per minute (cpm) against concentration (of quorum sensing molecules or vehicle) is shown in FIG. 9. As can be seen from FIG. 9, both PQS and OdDHL optimally inhibited cell proliferation in a dose dependent manner in a concentration range of from above about 10 µM to about 30 µM in this experiment.

III.II The concanavalin A-induced cell proliferation of human peripheral blood mononuclear cells (hPBMC) was tracked, in accordance with the procedure generally described in I.II above, in the presence of 6.25 µM OdDHL, a concentration at which OdDHL is considered to be inactive in view of the fact that it achieves an effect only slightly better than the control. Cell proliferation was, separately, investigated in the presence of PQS in the concentration range of from 1.25 µM to 10 µM, considered to represent suboptimal concentrations of PQS. A further investigation into cell proliferation was carried out in the presence of a combination of OdDHL (at a concentration of 6.25 µM) and PQS at various concentrations in the range of from 1.25 µM to 10 µM. Plots of counts per minute (cpm) against PQS concentration are shown in FIG. 10. As can be seen in this Figure, the effect achieved using the combination of 6.25 µM OdDHL and PQS in the range of from 1.25)µM to 10 µM is greater than the sum of the individual effects achieved using the OdDHL alone and the PQS alone.

The proliferation of hPBMC stimulated with 1 µg/ml concanavalin A was investigated in accordance with the procedure set out in I.II above, in the presence of various concentrations of different quorum sensing molecules (PQS, OdDHL and OHHL) and, as a control, the vehicle dimethyl sulphoxide (DMSO) on its own. Plots of counts per minute (cpm) against the concentration of the quorum sensing molecules and the vehicle are shown in FIG. 11. As can be seen from FIG. 11, each of PQS and OdDHL optimally inhibited the concanavalin stimulated hPBMC in a dose dependent manner at higher concentrations, for example above 10 µM.

IV Human PBMC Assays

Optimisation of Cell Culture Conditions

In cell culture assays the number of human peripheral blood mononuclear cells (hPBMC) used was initially optimised to 100,000 cells per well. Optimal dosing of anti-CD3 and anti-CD28 antibodies, used in the cell proliferation assays and to induce the release of IL-2, was determined from antibody titration curves.

IV.I Cell Proliferation of hPBMC Stimulated with Anti-CD3 and Anti-CD28

Anti-CD3 and anti-CD28 antibodies were used to assess the effect of quorum sensing signal molecules (PQS, OdDHL and OHHL) on T-cell proliferation and IL-2 secretion. Proliferation was assessed by the incorporation of [$^3$H]-thymidine into the DNA of PBMC and the release of cytokines in the culture supernatants was determined by 'sandwich' ELISA. Blood specimens were obtained with consent from four healthy human volunteers (aged between 20 and 50 years). Human PBMC were isolated from heparinised whole blood by buoyant density centrifugation over Histopaque 1077 (Sigma, Poole, UK) at 600 g for 20 minutes. PBMC harvested from the 'buffy' layers were washed twice with RPMI 1640 medium and resuspended in complete cell culture medium (CTCM) consisting of RPMI 1640 medium with 5% FCS, 2 mM L-glutamine, and $5 \times 10^{-5}$ M 2-mercaptoethanol. The quorum sensing molecules, of which stock solutions of 0.1 M were soluble in DMSO, were initially diluted into CTCM and then tested in triplicate wells at concentrations ranging from 0.78125 to 100 µM in 200 µl of CTCM, containing 100,000 hPBMC which were challenged with 100 ng/ml of mouse anti-human CD3 monoclonal antibody (clone UCHT1; BD Pharmingen, UK) and 5 µg/ml of mouse anti-human CD28 monoclonal antibody (clone CD28.2; BD Pharmingen, UK). hPBMC were incubated for 24 h at 37° C. in 5% $CO_2$-air and 50 µl of culture supernatants were removed for the determination of IL-2 (see IV.II below). The cells were returned for a further 24 h culture, followed by pulsing with 0.25 µCi [$^3$H]-thymidine (Amersham) in 10 µl volume made up in RPMI 1640 medium. After a further incubation of 24 h, cells were harvested onto 96-well filter plates (Unifilter Filtermate Harvester™, Packard Bioscience Ltd, UK). Following the addition of 25 µl of scintillant (MicroScint-O™; Packard Bioscience Ltd. UK) to each well in the filter plates, the radioactivity in the filters was measured with a β-scintillation counter (TopCount™, Packard Bioscience Ltd, UK) according to manufacturer's specifications. The inhibitory effect of a compound (quorum sensing molecule or control) being tested on cell proliferation was indicated by a reduction in counts per minute (cpm). The results for hPBMC from Donors I, II, III and IV are given in FIG. 14 which shows plots of cpm against test compound concentration (µM). Data represent means of triplicate wells±standard deviations.

As can be seen from FIG. 14, both PQS and OdDHL inhibited, in a dose dependent manner, the proliferation of hPBMC stimulated via CD3 and CD28. PQS was consistently more potent than OdDHL.

IV.II IL-2 Production From Anti-CD3 and Anti-CD28 Stimulated hPBMC

When T cells in hPBMC are challenged with anti-CD3 and anti-CD28 antibodies, the cytokine IL-2 is released into the culture supernatants. The levels of cytokine produced in the culture supernatants after 24 h were determined in a 'sandwich' ELISA. Briefly, 96-well Nunc MaxiSorp (Life Technologies, Paisley, UK) plates were coated with 50 µl of a 2 µg/ml solution of 'capture' mouse anti-human IL-2 monoclonal antibody (BD Pharmingen, UK) in 0.05 M carbonate/bicarbonate buffer, pH 9.6 overnight at 4° C. After washing the plates three times with PBS-Tween, which contained phosphate buffered saline (PBS) and 0.5% (vol/vol) Tween 20 (Sigma, Poole, UK), the plates were blocked with 1% (wt/vol) bovine serum albumin (BSA) (Sigma, Poole, UK) at room temperature for 2 h. Following three washes with PBS-Tween, 50 µl of cell culture supernatants were added and incubated overnight at 4° C.; standard human IL-2 concentrations (BD Pharmingen, UK) ranging from 7.8125 to 500 pg/ml were included for each plate. After four washes with PBS-Tween, 50 µL of a 2 µg/ml solution of biotinylated mouse anti-human IL-2 monoclonal antibody (BD Pharmingen, UK) diluted in 1% BSA in PBS-Tween were added and incubated at room temperature for 1 h. Following four washes, the bound biotinylated antibody was detected with 50 µl of a 1:1,000 dilution of streptavidin-peroxidase (BD Pharmingen, UK). At the end of an hour incubation at room temperature, the plates were thoroughly washed six times with PBS-Tween and the assay was developed by the addition of 100 µl of 0.1 mg/ml of tetramethyl benzidine substrate (Sigma, Poole, UK) in 0.1 M sodium acetate buffer, pH 6 containing 0.03% $H_2O_2$ (Sigma, Poole, UK). The enzyme reaction was stopped with 50 µl of 2.5 M $H_2SO_4$ after a development of 10 minutes at room temperature and the colourimetric development was read at 450 nm with a spectrophotometric 96-well plate reader (Dynex). The concentrations of IL-2 in the culture supernatants were determined by extrapolation from the reference standard IL-2 curve.

The results are given in FIG. 15 which shows the plots of IL-2 concentration (pg/ml), as determined by ELISA, against test compound (PQS, OdDHL, OHHL or the vehicle, DMSO) concentration (µM). Data represent means of triplicate wells±standard deviations.

As can be seen from FIG. 15, OdDHL, but not PQS, inhibited in a dose dependent manner the release of IL-2 when hPBMC from each of the four donors were stimulated via CD3 and CD28.

The results given in FIG. 14 show that both PQS and OdDHL inhibit the proliferation of stimulated hPBMC whereas the results given in FIG. 15 indicate that OdDHL, but not PQS, inhibits the release of IL-2 from stimulated hPBMC. It is clear from these data that PQS and OdDHL act at different stages of T cell activation, with OdDHL acting upstream of IL-2 secretion and PQS acting downstream. This is an unexpected result, as these compounds are bacterial signal molecules, and the effects on T cell activation are reminiscent of those seen with cyclosporin A and rapamycin, which is indicative of the presence of different molecular targets for each bacterial compound.

The invention claimed is:

1. A composition comprising at least one compound of the formula I

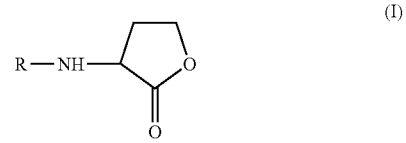

in which R is an acyl group of the formula II

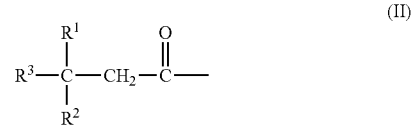

wherein one of $R^1$ and $R^2$ is H and the other is selected from $OR^4$, $SR^4$ and $NHR^4$, wherein $R^4$ is H or 1-6C alkyl, or $R^1$ and $R^2$ together with the carbon atom to which they are joined form a keto group, and $R^3$ is a straight or branched chain, saturated or unsaturated aliphatic hydrocarbyl group containing from 8 to 11 carbon atoms and is optionally substituted by one or more substituent groups selected from halo, 1-6C alkoxy, carboxy, 1-6C alkoxycarbonyl and $NR^5R^6$ wherein each of $R^5$ and $R^6$ is selected from H and 1-6C alkyl or $R^5$ and $R^6$ together with the N atom form a morpholino or piperazino group, or any enantiomer thereof, together with at least one compound of the formula III

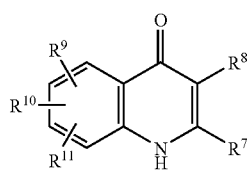

wherein $R^7$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and $NR^{12}R^{13}$, wherein each of $R^{12}$ and $R^{13}$ is independently selected from H and 1-6C alkyl or $R^{12}$ and $R^{13}$ together with the N atom to which they are attached form a saturated heterocyclic group selected from piperidino, piperazino and morpholino; $R^8$ is a group selected from H, —OH, halo, —CHO, —$CO_2H$ and $CONHR^{14}$ wherein $R^{14}$ is H or a 1-6C alkyl; each of $R^9$, $R^{10}$ and $R^{11}$ is independently selected from H, —$CH_3$, —$OCH_3$ and halo; or a non-toxic pharmaceutically-acceptable salt thereof.

2. A composition according to claim 1, wherein the group R in formula 1 is selected from

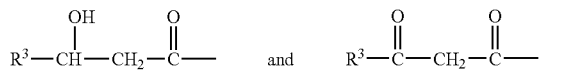

where $R^3$ is as defined in claim 1.

3. A composition according to either claim 1 or claim 2, wherein the group $R^3$ is an 18-11C straight or branched chain alkyl group optionally substituted by a substituent from bromo, carboxy and methoxycarbonyl.

4. A composition according to claim 3, wherein the $R^3$ group is such that the group R in formula I is selected from;
- 3-oxoundecanoyl;
- 11-bromo-3-oxoundecanoyl;
- 10-methyl-3-oxoundecanoyl;
- 6-methyl-3-oxoundecanoyl;
- 3-hydroxydodecanoyl;
- 12-bromo-3-oxododecanoyl;
- 3-oxododecanoyl;
- 3-oxotridecanoyl;
- 13-bromo-3-oxododecanoyl;
- 3-hydroxytetradecanoyl;
- 3-oxotetradecanoyl;
- 14-bromo-3-oxotetradecanoyl; and
- 13-methoxycarbonyl-3-oxotridecanoyl.

5. A composition according to either claim 1 or claim 2, wherein the group the $R^3$ is an 8-11C straight or branched chain alkenyl group optionally substituted by a substituent selected from bromo, carboxy and methoxycarbonyl.

6. A composition according to claim 5, wherein the $R^3$ group is such that the group R in formula I is selected from;
- 3-oxo-12-tridecenoyl;
- 3-oxo-7-tetradecenoyl;
- 3-hydroxy-7-tetradecenoyl;
- 3-oxo-9-tetradecenoyl;
- 3-hydroxy-9-tetradecenoyl;
- 3-oxo-10-tetradecenoyl;
- 3-hydroxy-10-tetradecenoyl;
- 3-oxo-11-tetradecenoyl;
- 3-hydroxy-11-tetradecenoyl;
- 3-oxo-13-tetradecenoyl; and
- 3-hydroxy-13-tetradecenoyl.

7. A composition according to claim 1, wherein in the compound of formula III the group $R^7$ is a straight chain alkyl group having from 3 to 13 carbon atoms.

8. A composition according to claim 7, wherein $R^7$ is n-heptyl.

9. A composition according to claim 1, wherein in the compound of the formula III the group $R^8$ is OH.

10. A composition according to claim 9, wherein the compound of the formula III is 2-n-heptyl-3-hydroxy-4(1H)-quinolone.

11. A composition according to claim 1, wherein the group $R^3$ is selected from the group consisting of 8-11C straight of branched chain alkyl and 8-11C straight or branched chain alkenyl, either chain being optionally substituted by one or more substituent groups selected from halo, 1-6C alkoxy, carboxy, 1-6C alkoxycarbonyl and $NR^5R^6$ wherein each of R5 and R6 is selected from H and 1-6C alkyl or $R^5$ and $R^6$ together with the N atom form a morpholino or piperazino group, or any enantiomer thereof.

12. A method of treating an autoimmune disease of a living animal body, which method comprises administering to the living animal bodyat least one compound of the formula I

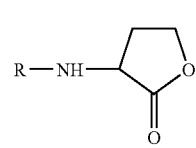

in which R is an acyl group of the formula II

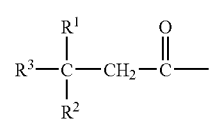

wherein one of $R^1$ and $R^2$ is H and the other is selected from $OR^4$, $SR^4$ and $NHR^4$, wherein $R^4$ is H or 1-6C alkyl, or $R^1$ and $R^2$ together with the carbon atom to which they are joined form a keto group, and $R^3$ is a straight or branched chain, saturated or unsaturated aliphatic hydrocarbyl group containing from 8 to 11 carbon atoms and is optionally substituted by one or more substituent groups selected from halo, 1-6C alkoxy, carboxy, 1-6C alkoxycarbonyl and $NR^5R^6$ wherein each of $R^5$ and $R^6$ is selected from H and 1-6C alkyl or $R^5$ and $R^6$ together with the N atom form a morpholino or piperazino group, or any enantiomer thereof, and at least one compound of the formula III

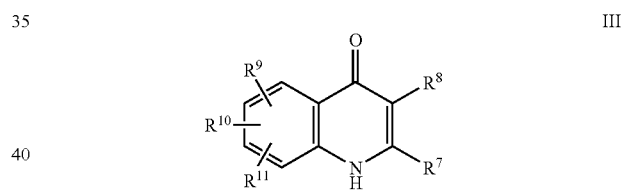

wherein $R^7$ is a straight or branched chain, saturated or ethylenically-unsaturated aliphatic hydrocarbyl group containing from 1 to 18 carbon atoms which may optionally be substituted by one or more substituent groups selected from halo, 1-6C alkoxy, carboxy, 1-6C alkoxycarbonyl and $NR^{12}R^{13}$, wherein each of $R^{12}$ and $R^{13}$ is independently selected from H and 1-6C alkyl or $R^{12}$ and $R^{13}$ together with the N atom to which they are attached form a saturated heterocyclic group selected from piperidino, piperazino and morpholino; $R^8$ is a group selected from H,—OH, halo, —CHO, —$CO_2H$ and $CONHR^{14}$ wherein $R^{14}$ is H or a 1-6C alkyl; each of $R^9$, $R^{10}$ and $R^{11}$ is independently selected from H, —$CH_3$, —$OCH_3$ and halo; or a non-toxic pharmaceutically-acceptable salt thereof.

13. A method according to claim 12 wherein the group R in formula I is selected from

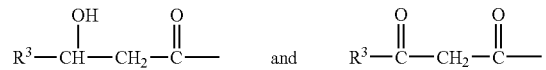

where $R^3$ is as defined in claim 1.

14. A method according to either claim 12 or claim 13, wherein the group $R^3$ is an 8-11C straight or branched chain alkyl group optionally substituted by a substituent selected from bromo, carboxy and methoxycarbonyl.

15. A method according to claim 14, wherein the $R^3$ group is such that the group R formula I is selected from;
3-oxoundecanoyl;
11-bromo-3-oxoundecanoyl;
10-methyl-3-oxoundecanoyl;
6-methyl-3-oxoundecanoyl;
3-hydroxydodecanoyl;
12-bromo-3-oxododecanoyl;
3-oxododecanoyl;
3-oxotridecanoyl;
13-bromo-3-oxododecanoyl;
3-hydroxytetradecanoyl;
3-oxotetradecanoyl;
14-bromo-3-oxotetradecanoyl; and
13-methoxycarbonyl-3-oxotridecanoyl.

16. A method according to either claim 12 or claim 13, wherein the group $R^3$ is an 8-11C straight or branched chain alkenyl group optionally substituted by a substituent selected from bromo, carboxy and methoxycarbonyl.

17. A method according to claim 16, wherein the $R^3$ group is such that the group R in formula I is selected from;
3-oxo-7-tetradecenoyl;
3-hydroxy-7-tetradecenoyl;
3-oxo-9-tetradecenoyl;
3-hydroxy-9-tetradecenoyl;
3-oxo-10-tetradecenoyl;
3-hydroxy-10-tetradecenoyl;
3-oxo-11-tetradecenoyl;
3-hydroxy-11-tetradecenoyl;
3-oxo-13-tetradecenoyl; and
3-hydroxy-13-tetradecenoyl.

18. A method according to claim 12, wherein in the compound of the formula ill the group $R^7$ is a straight chain alkyl group having from 3 to 13 carbon atoms.

19. A method according to claim 18, wherein R7 is n-heptyl.

20. A method according to claim 12, wherein in the compound of the formula III the group $R^8$ is OH.

21. A method according to claim 20, wherein the compound of the formula III is 2-n-heptyl-3-hydroxy-4(1H)-quinolone.

22. A method according to claim 12, wherein the compounds of the formula I and III are administered to the animal body together.

23. A method according to claim 12, wherein at least one compound of the formula I is administered to the animal body and then at least one compound of the formula III is administered to the animal body.

24. A method according to claim 12, wherein at least one compound of the formula III is administered to the animal body and then at least one compound of the formula I is administered to the animal body.

25. A method according to claim 12 wherein the autoimmune disease is selected from psoriasis, multiple sclerosis and rheumatoid arthritis.

* * * * *